(12) United States Patent
Otten et al.

(10) Patent No.: US 6,479,436 B1
(45) Date of Patent: Nov. 12, 2002

(54) HETAROYL CYCLOHEXANEDIONE DERIVATIVES WITH HERBICIDAL EFFECT

(75) Inventors: Martina Otten, Ludwigshafen; Norbert Götz, Worms; Wolfgang von Deyn, Neustadt; Stefan Engel, Idstein; Uwe Kardorff, Mannheim; Peter Plath, Frankenthal; Regina Luise Hill, Speyer; Matthias Witschel, Ludwigshafen; Ulf Misslitz, Neustadt; Karl-Otto Westphalen, Speyer; Helmut Walter, Obrigheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/254,973

(22) PCT Filed: Sep. 9, 1997

(86) PCT No.: PCT/EP97/04894

§ 371 (c)(1),
(2), (4) Date: Mar. 17, 1999

(87) PCT Pub. No.: WO98/12180

PCT Pub. Date: Mar. 26, 1998

(30) Foreign Application Priority Data

Sep. 20, 1996 (DE) .......................................... 196 38 486

(51) Int. Cl.[7] ...................... A01N 43/42; C07D 215/14; C07D 215/18; C07D 215/22; C07D 217/22
(52) U.S. Cl. ...................... 504/247; 546/141; 546/142; 546/146; 546/153; 546/156; 546/166; 546/168
(58) Field of Search ................................. 546/166, 168, 546/153, 156, 146, 141; 504/247

(56) References Cited

U.S. PATENT DOCUMENTS

| 4,909,835 A | | 3/1990 | Tobler .......................... 70/103 |
| 4,995,902 A | | 2/1991 | Brunner ......................... 71/94 |
| 5,480,858 A | * | 1/1996 | Sakamoto ................... 504/228 |
| 5,744,610 A | * | 4/1998 | Barton ......................... 548/217 |
| 5,952,266 A | * | 9/1999 | Tseng .......................... 504/288 |
| 6,040,274 A | | 3/2000 | Kast et al. ................... 504/348 |

FOREIGN PATENT DOCUMENTS

| CA | 2093105 | 10/1993 |
| EP | 283 261 | 9/1988 |
| WO | 97/01550 | 1/1997 |
| WO | 97/08164 | 3/1997 |

* cited by examiner

*Primary Examiner*—Evelyn Mei Huang
(74) *Attorney, Agent, or Firm*—Keil & Weinkauf

(57) ABSTRACT

Hetaroyl derivatives of the formula I

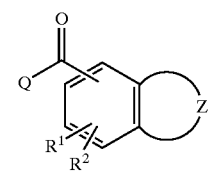

where:

$R^1$ and $R^2$ are each hydrogen, nitro, halogen, cyano, thiocyanato, hydroxyl, mercapto, $C_1$–$C_6$-alkyl, $C_1$–$C_6$-alkoxy, $C_1$–$C_6$-alkylthio, $C_1$–$C_6$-alkylsulfinyl, $C_1$–$C_6$-alkylsulfonyl or $C_1$–$C_6$-alkoxysulfonyl, where the last 6 radicals may be substituted and/or functionalized; phenyl, phenoxy, phenylthio, phenylsulfinyl or phenylsulfonyl, where the last 5 radicals may be substituted;

Z is an unsubstituted or substituted four-membered unsaturated, partially or fully saturated chain consisting of three carbons and one nitrogen;

Q is unsubstituted or substituted cyclohexane-1,3-dione linked at position 2;

and their agriculturally useful salts. A process for preparing the hetaroyl derivatives, compositions comprising them, and the use of these derivatives or these compositions comprising them for controlling undesirable plants.

18 Claims, No Drawings

HETAROYL CYCLOHEXANEDIONE DERIVATIVES WITH HERBICIDAL EFFECT

This application is the national phase of PCT/EP97/04894 filed on Sept. 9, 1997.

The present invention relates to novel hetaroyl derivatives of the formula I

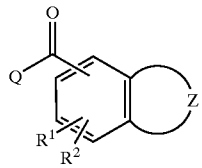

where:

$R^1$ and $R^2$ are each hydrogen, nitro, halogen, cyano, thiocyanato, hydroxyl, mercapto, $C_1$–$C_6$-alkyl, $C_1$–$C_6$-haloalkyl, $C_2$–$C_6$-alkenyl, $C_2$–$C_6$-alkynyl, $C_1$–$C_6$-alkoxy, $C_1$–$C_6$-haloalkoxy, $C_2$–$C_6$-alkenyloxy, $C_2$–$C_6$-alkynyloxy, $C_1$–$C_6$-alkylthio, $C_1$–$C_6$-haloalkylthio, $C_2$–$C_6$-alkenylthio, $C_2$–$C_6$-alkynylthio, $C_1$–$C_6$-alkylsulfinyl, $C_1$–$C_6$-haloalkylsulfinyl, $C_2$–$C_6$-alkenylsulfinyl, $C_2$–$C_6$-alkynylsulfinyl, $C_1$–$C_6$-alkylsulfonyl, $C_1$–$C_6$-haloalkylsulfonyl, $C_2$–$C_6$-alkenylsulfonyl, $C_2$–$C_6$-alkynylsulfonyl, $C_1$–$C_6$-alkoxysulfonyl, $C_1$–$C_6$-haloalkoxysulfonyl, $C_2$–$C_6$-alkenyloxysulfonyl, $C_2$–$C_6$-alkynyloxysulfonyl, phenyl, phenyloxy, phenylthio, phenylsulfinyl or phenylsulfonyl, where the last five substituents may be partially or fully halogenated and may carry one to three of the following groups:
nitro, cyano, hydroxyl, $C_1$–$C_4$-alkyl, $C_1$–$C_4$-haloalkyl, $C_1$–$C_4$-alkoxy, $C_1$–$C_4$-haloalkoxy;

Z is a building block from the group consisting of $Z^1$ to $Z^{12}$.

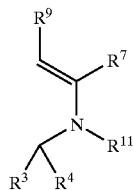

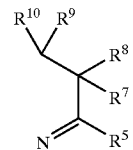

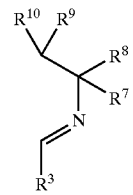

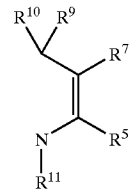

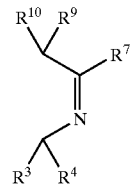

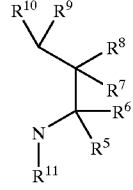

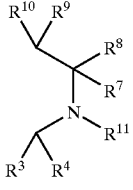

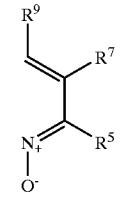

-continued

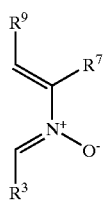

where $R^3$, $R^5$, $R^7$ and $R^9$ are each hydrogen, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkythio, nitro, cyano, hydroxyl, mercapto, $C_2$-$C_4$-alkenyl, $C_2$-$C_4$-alkynyl, $C_2$-$C_4$-alkenyloxy, $C_2$-$C_4$-alkynyloxy, $C_2$-$C_4$-alkenylthio, $C_2$-$C_4$-alkynylthio, $C_1$-$C_4$-alkylsulfinyl, $C_1$-$C_4$-haloalkylsulfinyl, $C_2$-$C_4$-alkenylsulfinyl, $C_2$-$C_4$-alkynylsulfinyl, $C_1$-$C_4$-alkylsulfonyl, $C_1$-$C_4$-haloalkylsulfonyl, $C_2$-$C_4$-alkenylsulfonyl, $C_2$-$C_4$-alkynylsulfonyl, $C_1$-$C_4$-alkoxysulfonyl, $C_1$-$C_4$-haloalkoxysulfonyl, $C_2$-$C_4$-alkenyloxysulfonyl, $C_2$-$C_4$alkynyloxysulfonyl, $-NR^{12}R^{13}$, $-CO_2R^{12}$, $-CONR^{12}R^{13}$, phenyl, phenoxy, phenylthio, phenylsulfinyl or phenylsulfonyl, where the last five substituents may be partially or fully halogenated and may carry one to three of the following groups: nitro, cyano, hydroxyl, $C_1$-$C_4$-alkyl, $C_1$-$C_4$-haloalkyl, $C_1$-$C_4$-alkoxy, $C_1$-$C_4$-haloalkoxy;

$R^4$, $R^6$, $R^8$ and $R^{10}$ are each hydrogen, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkylthio;

or a $-CR^3R^4-$, $-CR^5R^6-$, $-CR^7R^8-$ or $-CR^9R^{10}-$ unit may be replaced by $C=O$ or $C=NR^{13}$;

$R^{11}$ is hydrogen, $C_1$-$C_6$-alkyl, $C_1$-$C_6$-haloalkyl, $C_3$-$C_6$-alkenyl, $C_3$-$C_6$-alkynyl, $C_1$-$C_6$-alkylcarbonyl, $C_1$-$C_6$-haloalkylcarbonyl, $-CO_2R^{12}$, $-CONR^{12}R^{13}$ or $SO_2R^{12}$;

$R^{12}$ is hydrogen, $C_1$-$C_6$-alkyl, $C_1$-$C_6$-haloalkyl, $C_3$-$C_6$-alkenyl, $C_3$-$C_6$-alkynyl or phenyl, where the last radical may be partially or fully halogenated and may carry one to three of the following radicals: nitro, cyano, hydroxyl, $C_1$-$C_4$-alkyl, $C_1$-$C_4$-haloalkyl, $C_1$-$C_4$-alkoxy, $C_1$-$C_4$-haloalkoxy;

$R^{13}$ is $C_1$-$C_6$-alkoxy, $C_1$-$C_6$-haloalkoxy, $C_3$-$C_6$-alkenyloxy, $C_3$-$C_6$-alkynyloxy or one of the radicals mentioned under $R^{12}$;

Q is an unsubstituted or substituted cyclohexane-1,3-dione ring linked through position 2;

and their agriculturally useful salts.

The invention additionally relates to processes for preparing compounds of the formula I, to compositions comprising compounds of the formula I and to the use of these derivatives or to compositions comprising these derivatives for controlling harmful plants.

2-Hetaroylcyclohexanediones are known from the literature, for example from EP-A 283 261.

However, the herbicidal properties of these prior art compounds and their compatibility with crop plants are not entirely satisfactory. It is therefore an object of the present invention to provide novel, in particular herbicidally active, compounds with improved properties.

We have found that this object is achieved by the hetaroyl derivatives of the formula I and their herbicidal action.

Furthermore, the invention provides herbicidal compositions comprising the compounds I and having a very good herbicidal activity. Additionally, the invention provides processes for preparing these compositions and methods for controlling undesirable plant growth using the compounds I.

Depending on the substitution pattern, the compounds of the formula I may contain one or more chiral centers and, if this is the case, be present as enantiomers or as mixtures of diastereomer. The invention provides the pure enantiomers or diastereomers and mixtures thereof.

The compounds of the formula I may also be present in the form of their agriculturally useful salts, the kind of salt generally not being important. The salts of those cations or the acid addition salts of those acids whose cations or anions, respectively, do not adversely affect the herbicidal activity of the compounds I are generally suitable.

Suitable cations are in particular ions of the alkali metals, preferably lithium, sodium and potassium, of the alkaline earth metals, preferably calcium and magnesium, and of the transition metals, preferably manganese, copper, zinc and iron, and ammonium which may, if desired, carry one to four $C_1$-$C_4$-alkyl substituents and/or one phenyl or benzyl substituent, preferably diisopropyl-ammonium, tetramethylammonium, tetrabutylammonium, trimethylbenzylammonium, and further phosphonium ions and sulfonium ions, preferably tri($C_1$-$C_4$-alkyl)sulfonium and sulfoxonium ions, preferably tri($C_1$-$C_4$-alkyl)sulfoxonium. Anions of useful acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of $C_1$-$C_4$-alkanoic acids, preferably formate, acetate, propionate and butyrate.

Particular preference is given to the compounds of the formula I according to the invention where the variable Q is a cyclohexane-1,3-dione ring, linked through position 2, of the formula II

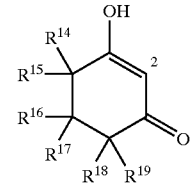

II where II also represents the tautomeric forms II' and II''

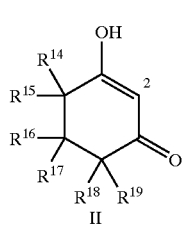 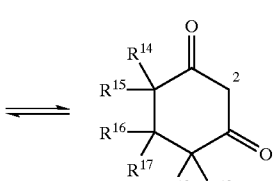 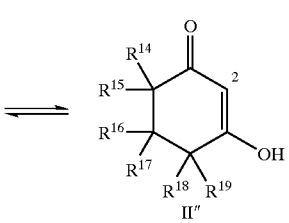

where $R^{14}$, $R^{15}$, $R^{17}$ and $R^{19}$ are each hydrogen or $C_1$–$C_4$-alkyl;

$R^{16}$ is hydrogen, $C_1$–$C_4$-alkyl or $C_3$–$C_4$-cycloalkyl, where the last two groups may carry one to three of the following substituents:
halogen, $C_1$–$C_4$-alkylthio or $C_1$–$C_4$-alkoxy; or
is tetrahydropyran-3-yl, tetrahydropyran-4-yl, tetrahydrothiopyran-3-yl, 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, where the last 6 radicals may be substituted by one to three $C_1$–$C_4$-alkyl radicals;

$R^{18}$ is hydrogen, $C_1$–$C_4$-alkyl or $C_1$–$C_6$-alkoxycarbonyl; or $R^{16}$ and $R^{19}$ together form a bond or a three- to six-membered carbocyclic ring; or the —$CR^{16}R^{17}$— unit may be replaced by C=O.

The organic moieties mentioned for the substituents $R^1$–$R^{19}$ or as radicals on phenyl rings represent collective terms for lists of the individual group members. All hydrocarbon chains, ie. all the alkyl, haloalkyl, alkoxy, haloalkoxy, alkylthio, haloalkylthio, alkylsulfinyl, haloalkylsulfinyl, alkylsulfonyl, haloalkylsulfonyl, alkoxysulfonyl, haloalkoxysulfonyl, alkylcarbonyl, haloalkylcarbonyl, alkoxycarbonyl, alkenyl, alkenyloxy, alkenylthio, alkenylsulfinyl, alkenylsulfonyl, alkenyloxysulfonyl, alkynyl, alkynyloxy, alkynylthio, alkynylsulfinyl, alkynylsulfonyl and alkynyloxysulfonyl moieties, may be straight-chain or branched. Unless stated otherwise, preference is given to halogenated substituents carrying one to five identical or different halogens. Halogen is in each case fluorine, chlorine, bromine or iodine.

Furthermore, the following moieties represent, for example:

$C_1$–$C_4$-alkyl and the alkyl moieties of $C_1$–$C_4$-alkylcarbonyl: methyl, ethyl, propyl, 1-methylethyl, butyl, 1-methylpropyl, 2-methylpropyl and 1,1-dimethylethyl;

$C_1$–$C_6$-alkyl and the alkyl moieties of $C_1$–$C_6$-alkylcarbonyl: $C_1$–$C_4$-alkyl as mentioned above, and pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_4$-haloalkyl and the haloalkyl moieties of $C_1$–$C_4$-haloalkylcarbonyl: a $C_1$–$C_4$-alkyl radical as mentioned above which is partially or fully substituted by fluorine, chlorine, bromine and/or iodine, ie. for example chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_6$-haloalkyl and the haloalkyl moieties of $C_1$–$C_6$-haloalkylcarbonyl: $C_1$–$C_4$-haloalkyl as mentioned above, and 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_1$–$C_4$-alkoxy and the alkoxy moieties in $C_1$–$C_4$-alkoxycarbonyl; methoxy, ethoxy, propoxy, 1-methylethoxy, butoxy, 1-methylpropoxy, 2-methylpropoxy and 1,1-dimethylethoxy;

$C_1$–$C_6$-alkoxy and the alkoxy moieties in $C_1$–$C_6$-alkoxycarbonyl: $C_1$–$C_4$-alkoxy as mentioned above, and pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, ie. for example fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$–$C_6$-haloalkoxy: $C_1$–$C_4$-haloalkoxy as mentioned above, and 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

$C_1$–$C_4$-alkylthio: methylthio, ethylthio, propylthio, 1-methylethylthio, butylthio, 1-methylpropylthio, 2-methylpropylthio and 1,1-dimethylethylthio;

$C_1$–$C_6$-alkylthio: $C_1$–$C_4$-alkylthio as mentioned above, and pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$–$C_4$-haloalkylthio: a $C_1$–$C_4$-alkylthio radical as mentioned above which is partially or fully substituted by fluorine, chlorine, bromine and/or iodine, ie. for example fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio and nonafluorobutylthio;

$C_1$–$C_6$-haloalkylthio: $C_1$–$C_4$-haloalkylthio as mentioned above, and 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio and dodecafluorohexylthio;

$C_1$–$C_4$-alkylsulfinyl ($C_1$–$C_4$-alkyl-S(=O)—): methylsulfinyl, ethylsulfinyl, propylsulfinyl, 1-methylethylsulfinyl, butylsulfinyl, 1-methylpropylsulfinyl, 2-methylpropylsulfinyl and 1,1-dimethylethylsulfinyl;

$C_1$–$C_6$-alkylsulfinyl: $C_1$–$C_4$-alkylsulfinyl as mentioned above, and pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$–$C_4$-haloalkylsulfinyl: a $C_1$–$C_4$-alkylsulfinyl radical as mentioned above which is partially or fully substituted by fluorine, chlorine, bromine and/or iodine, ie. fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl and nonafluorobutylsulfinyl;

$C_1$–$C_6$-haloalkylsulfinyl: $C_1$–$C_4$-haloalkylsulfinyl as mentioned above, and 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl and dodecafluorohexylsulfinyl;

$C_1$–$C_4$-alkylsulfonyl ($C_1$–$C_4$-alkyl-S(=O)$_2$—): methylsulfonyl, ethylsulfonyl, propylsulfonyl, 1-methylethylsulfonyl, butylsulfonyl, 1-methylpropylsulfonyl, 2-methylpropylsulfonyl and 1,1-dimethylethylsulfonyl;

$C_1$–$C_6$-alkylsulfonyl: $C_1$–$C_4$-alkylsulfonyl as mentioned above, and pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, 1,1-dimethylpropylsulfonyl, 1,2-dimethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$–$C_4$-haloalkylsulfonyl: a $C_1$–$C_4$-alkylsulfonyl radical as mentioned above which is partially or fully substituted by fluorine, chlorine, bromine and/or iodine, ie. fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2,2,2-trichloroethylsulfonyl, 2-chloro-2-fluoroethylsulfonyl, 2-chloro-2,2-difluoroethylsulfonyl, 2,2-dichloro-2-fluoroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(choromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl and nonafluorobutylsulfonyl;

$C_1$–$C_6$-haloalkylsulfonyl: $C_1$–$C_4$-haloalkylsulfonyl as mentioned above, and 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl and dodecafluorohexylsulfonyl;

$C_1$–$C_4$-alkoxysulfonyl: methoxysulfonyl, ethoxysulfonyl, propoxysulfonyl, 1-methylethoxysulfonyl, butoxysulfonyl, 1-methylpropoxysulfonyl, 2-methylpropoxysulfonyl and 1,1-dimethylethoxysulfonyl;

$C_1$–$C_6$-alkoxysulfonyl: $C_1$–$C_4$-alkoxysulfonyl as mentioned above, and pentoxysulfonyl, 1-methylbutoxysulfonyl, 2-methylbutoxysulfonyl, 3-methylbutoxysulfonyl, 1,1-dimethylpropoxysulfonyl, 1,2-dimethylpropoxysulfonyl, 2,2-dimethylpropoxysulfonyl, 1-ethylpropoxysulfonyl, hexoxysulfonyl, 1-methylpentoxysulfonyl, 2-methylpentoxysulfonyl, 3-methylpentoxysulfonyl, 4-methylpentoxysulfonyl, 1,1-dimethylbutoxysulfonyl, 1,2-dimethylbutoxysulfonyl, 1,3-dimethylbutoxysulfonyl, 2,2-dimethylbutoxysulfonyl, 2,3-dimethylbutoxysulfonyl, 3,3-dimethylbutoxysulfonyl, 1-ethylbutoxysulfonyl, 2-ethylbutoxysulfonyl, 1,1,2-trimethylpropoxysulfonyl, 1,2,2-trimethylpropoxysulfonyl, 1-ethyl-1-methylpropoxysulfonyl and 1-ethyl-2-methylpropoxysulfonyl;

$C_1$–$C_4$-haloalkoxysulfonyl: a $C_1$–$C_4$-alkoxysulfonyl radical as mentioned above which is partially or fully substituted by fluorine, chlorine, bromine and/or iodine, ie. for example fluoromethoxysulfonyl, difluoromethoxysulfonyl, trifluoromethoxysulfonyl, chlorodifluoromethoxysulfonyl, bromodifluoromethoxysulfonyl, 2-fluoroethoxysulfonyl, 2-chloroethoxysulfonyl, 2-bromoethoxysulfonyl, 2-iodoethoxysulfonyl, 2,2-difluoroethoxysulfonyl, 2,2,2-trifluoroethoxysulfonyl, 2-chloro-2-fluoroethoxysulfonyl, 2-chloro-2,2-difluoroethoxysulfonyl, 2,2-dichloro-2-fluoroethoxysulfonyl, 2,2,2-trichloroethoxysulfonyl, pentafluoroethoxysulfonyl, 2-fluoropropoxysulfonyl, 3-fluoropropoxysulfonyl, 2-chloropropoxysulfonyl, 3-chloropropoxysulfonyl, 2-bromopropoxysulfonyl, 3-bromopropoxysulfonyl, 2,2-difluoropropoxysulfonyl, 2,3-difluoropropoxysulfonyl, 2,3-dichloropropoxysulfonyl, 3,3,3-trifluoropropoxysulfonyl, 3,3,3-trichloropropoxysulfonyl, 2,2,3,3,3-pentafluoropropoxysulfonyl, heptafluoropropoxysulfonyl, 1-(fluoromethyl)-2-fluoroethoxysulfonyl, 1-(chloromethyl)-2-chloroethoxysulfonyl, 1-(bromomethyl)-2-bromoethoxysulfonyl, 4-fluorobutoxysulfonyl, 4-chlorobutoxysulfonyl, 4-bromobutoxysulfonyl and 4-iodobutoxysulfonyl;

$C_1$–$C_6$-haloalkoxysulfonyl: $C_1$–$C_4$-haloalkoxysulfonyl as mentioned above, and 5-fluoropentoxysulfonyl, 5-chloropentoxysulfonyl, 5-bromopentoxysulfonyl, 5-iodopentoxysulfonyl, undecafluoropentoxysulfonyl, 6-fluorohexoxysulfonyl, 6-chlorohexoxysulfonyl, 6-bromohexoxysulfonyl, 6-iodohexoxysulfonyl and dodecafluorohexoxysulfonyl;

$C_2$–$C_4$-alkenyl, and the alkenyl moieties of $C_2$–$C_4$-alkenyloxy, $C_2$–$C_4$-alkenylthio, $C_2$–$C_4$-alkenylsulfinyl, $C_2$–$C_4$-alkenylsulfonyl and $C_2$–$C_4$-alkenyloxysulfonyl: ethenyl, prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl and 2-methylprop-2-en-1-yl;

$C_2$–$C_6$-alkenyl, and the alkenyl moieties of $C_2$–$C6$-alkenyloxy, $C_2$–$C_6$-alkenylthio, $C_2$–$C_6$-alkenylsulfinyl, $C_2$–$C_6$-alkenylsulfonyl and $C_2$–$C_6$-alkenyloxysulfonyl: $C_2$–$C_4$-alkenyl as mentioned above, and penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl;

$C_2$–$C_4$-alkynyl and the alkynyl radicals of $C_2$–$C_4$-alkynyloxy, $C_2$–$C_4$-alkynylthio, $C_2$–$C_4$-alkynylsulfinyl, $C_2$–$C_4$-alkynylsulfonyl and $C_2$–$C_4$-alkynyloxysulfonyl: ethynyl, prop-1-yn-1-yl, prop-2-yn-1-yl, but-1-yn-1-yl, but-1-yn-3-yl, but-1-yn-4-yl and but-2-yn-1-yl;

$C_2$–$C_6$-alkynyl, and the alkynyl radicals of $C_2$–$C_6$-alkynyloxy, $C_2$–$C_6$-alkynylthio, $C_2$–$C6$-alkynylsulfinyl, $C_2$–$C_6$-alkynylsulfonyl and $C_2$–$C_6$-alkynyloxysulfonyl: $C_2$–$C_4$-alkynyl as mentioned above, and pent-1-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-1-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl;

$C_3$–$C_4$-cycloalkyl: cyclopropyl and cyclobutyl.

All phenyl rings are preferably unsubstituted or carry one to three halogens and/or a nitro group, a cyano radical, or a methyl, trifluoromethyl, methoxy or trifluoromethoxy substituent.

With respect to the use of the compounds of the formula I according to the invention as herbicides, the variables preferably have the meanings below, in each case on their own or in combination:

$R^1$ is nitro, halogen, cyano, thiocyanato, hydroxyl, mercapto, $C_1$–$C_6$-alkyl, $C_1$–$C_6$-haloalkyl, $C_2$–$C_6$-alkenyl, $C_2$–$C_6$-alkynyl, $C_1$–$C_6$-alkoxy, $C_1$–$C_6$-haloalkoxy, $C_2$–$C_6$-alkenyloxy, $C_2$–$C_6$-alkynyloxy, $C_1$–$C_6$-alkylthio, $C_1$–$C_6$-haloalkylthio, $C_2$–$C_6$-alkenylthio, $C_2$–$C_6$-alkynylthio, $C_1$–$C_6$-alkylsulfinyl, $C_1$–$C_6$-haloalkylsulfinyl, $C_2$–$C_6$-alkenylsulfinyl, $C_2$–$C_6$-alkynylsulfinyl, $C_1$–$C_6$-alkylsulfonyl, $C_1$–$C_6$-haloalkylsulfonyl, $C_2$–$C_6$-alkenylsulfonyl, $C_2$–$C_6$-alkynylsulfonyl, $C_1$–$C_6$-alkoxysulfonyl, $C_1$–$C_6$-haloalkoxysulfonyl, $C_2$–$C_6$-alkenyloxysulfonyl, $C_2$–$C_6$-alkynyloxysulfonyl, phenyl, phenyloxy, phenylthio, phenylsulfinyl or phenylsulfonyl, where the last five substituents may be partially or fully halogenated and may carry one to three of the following groups:

nitro, cyano, hydroxyl, $C_1$–$C_4$-alkyl, $C_1$–$C_4$-haloalkyl, $C_1$–$C_4$-alkoxy, $C_1$–$C_4$-haloalkoxy;

particularly preferably nitro, halogen, hydroxyl, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylsulfonyl, $C_1$–$C_6$-haloalkylsulfonyl or phenyl, where the last radical is unsubstituted or may carry one to three halogens and/or a nitro group, a cyano radical, or a methyl, trifluoromethyl, methoxy or trifluoromethoxy substituent;

especially preferably nitro, fluorine, chlorine, bromine, hydroxyl, methyl, ethyl, trifluoromethyl, methoxy, ethoxy, difluoromethoxy, trifluoromethoxy, methylsulfonyl, ethylsulfonyl, trifluoromethylsulfonyl, pentafluoroethylsulfonyl or phenyl;

$R^2$ is hydrogen, halogen or $C_1$–$C_6$-alkyl; particularly preferably hydrogen, chlorine, bromine or methyl;

Z is $Z^1$, $Z^2$, $Z^3$, $Z^4$, $Z^5$, $Z^6$, $Z^7$, $Z^8$, $Z^9$, $Z^{10}$, $Z^{11}$ or $Z^{12}$;

$R^3$, $R^5$, $R^7$ and $R^9$ are each hydrogen, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, nitro, cyano, hydroxyl, mercapto, $C_2$–$C_4$-alkenyl, $C_2$–$C_4$-alkynyl, $C_2$–$C_4$-alkenyloxy, $C_2$–$C_4$-alkynyloxy, $C_2$–$C_4$-alkenylthio, $C_2$–$C_4$-alkynylthio, $C_1$–$C_4$-alkylsulfinyl, $C_1$–$C_4$-haloalkylsulfinyl, $C_2$–$C_4$-alkenylsulfinyl, $C_2$–$C_4$-alkynylsulfinyl, $C_1$–$C_4$-alkylsulfonyl, $C_1$–$C_4$-haloalkylsulfonyl, $C_2$–$C_4$-alkenylsulfinyl, $C_2$–$C_4$-alkynylsulfonyl, $C_1$–$C_4$-alkoxysulfonyl, $C_1$–$C_4$-haloalkoxysulfonyl, $C_2$–$C_4$-alkenyloxysulfonyl, $C_2$–$C_4$-alkynyloxysulfonyl, —$NR^{12}R^{13}$, —$CO_2R^{12}$, —$CONR^{12}R^{13}$, phenyl, phenoxy, phenylthio, phenylsulfinyl or phenylsulfonyl, where the last five substituents may be partially or fully halogenated and may carry one to three of the following groups:

nitro, cyano, hydroxyl, $C_1$–$C_4$-alkyl, $C_1$–$C_4$-haloalkyl, $C_1$–$C_4$-alkoxy, $C_1$–$C_4$-haloalkoxy;

particularly preferably hydrogen, halogen, $C_1$–$C_4$-alkyl, $C_1$–$C_4$-haloalkyl, $C_1$–$C_4$-alkoxy, $C_1$–$C_4$-haloalkoxy, nitro, cyano, hydroxyl, $C_1$–$C_6$-alkoxycarbonyl or phenyl, where the last radical is unsubstituted or may carry one to three halogens and/or a nitro group, a cyano radical, or a methyl, trifluoromethyl, methoxy or trifluoromethoxy substituent;

especially preferably hydrogen, fluorine, chlorine, bromine, methyl, ethyl, trifluoromethyl, methoxy, ethoxy, trifluoromethoxy, difluoromethoxy, nitro, cyano, hydroxyl, methoxycarbonyl, ethoxycarbonyl or phenyl;

$R^4$, $R^6$, $R^8$ and $R^{10}$ are each hydrogen, halogen or $C_1$–$C_4$-alkyl; particularly preferably hydrogen, fluorine, chlorine, methyl or ethyl; especially preferably hydrogen;

$R^{11}$ is hydrogen, $C_1$–$C_6$-alkyl, $C_1$–$C_6$-haloalkyl, $C_1$–$C_6$-alkylcarbonyl, $C_1$–$C_6$-haloalkylcarbonyl, $C_1$–$C_6$-alkylsulfonyl, $C_1$–$C_6$-haloalkylsulfonyl or phenylsulfonyl, where the last phenyl radical may be substituted by a $C_1$–$C_4$-alkyl radical; particularly preferably methyl, ethyl, difluoromethyl, trifluoromethyl, methylcarbonyl, ethylcarbonyl, isopropylcarbonyl, trifluoromethylcarbonyl, methylsulfonyl, trifluoromethylsulfonyl, phenylsulfonyl or 4-methylphenylsulfonyl;

$R^{12}$ is hydrogen or $C_1$–$C_6$-alkyl; particularly preferably hydrogen, methyl or ethyl;

$R^{13}$ is hydrogen, $C_1$–$C_6$-alkyl, $C_1$–$C_6$-alkoxy, $C_3$–$C_6$-alkenyloxy or $C_3$–$C_6$-alkynyloxy; particularly preferably methyl, ethyl, methoxy, ethoxy, 2-propen-1-yloxy, 2-propyn-1-yloxy or 1-methyl-2-propyn-1-yloxy;

$R^{14}$, $R^{15}$, $R^{17}$ and $R^{19}$ are each hydrogen or $C_1$–$C_4$-alkyl; particularly preferably hydrogen, methyl or ethyl;

$R^{16}$ is hydrogen, $C_1$–$C_4$-alkyl or $C_3$–$C_4$-cycloalkyl, where the last two groups may carry one to three of the following substituents: halogen, $C_1$–$C_4$-alkoxy or $C_1$–$C_4$-alkylthio; tetrahydropyran-3-yl, tetrahydropyran-4-yl, tetrahydrothiopyran-3-yl, 1,3-dioxolan-2-yl, 1,3-dioxan-2-yl, 1,3-oxathiolan-2-yl, 1,3-oxathian-2-yl, 1,3-dithian-2-yl or 1,3-dithiolan-2-yl, where the last six groups may be unsubstituted or may carry up to three $C_1$–$C_4$-alkyl radicals; particularly preferably hydrogen, methyl, ethyl, cyclopropyl, di(methoxy)methyl, di(ethoxy)methyl, 2-ethylthiopropyl, tetrahydropyran-3-yl, tetrahydropyran-4-yl, 1,3-dioxolan-2-yl, 1,3-dioxan-2-yl, 5,5-dimethyl-1-3-dioxan-2-yl [sic], 1,3-oxathiolan-2-yl, 1,3-oxathian-2-yl, 1,3-dithiolan-2-yl, 5,5-dimethyl-1,3-dithian-2-yl or 1-methylthiocyclopropyl;

$R^{18}$ is hydrogen, $C_1$–$C_4$-alkyl or $C_1$–$C_4$-alkoxycarbonyl; particularly preferably hydrogen, methyl or methoxycarbonyl.

It is also possible for $R^{16}$ and $R^{19}$ to form a $\pi$ bond, thus giving rise to a double bond system.

If desired, the —$CR^{16}R^{17}$— unit may be replaced by C=O.

Preference is given to compounds of the formula I wherein the variable Z is $Z^1$, $Z^2$, $Z^{11}$ or $Z^{12}$.

Preference is also given to the compounds of the formula I wherein the variable Z is $Z^3$, $Z^4$, $Z^5$, $Z^6$, $Z^7$ or $Z^8$.

Preference is also given to the compounds of the formula I wherein the variable Z is $Z^9$ or $Z^{10}$.

Particular preference is given to compounds of the formulae Ia–Ic (Z=$Z^1$) and Id–Ie (Z=$Z^2$) and their N-oxides Ia'–Ic' (Z=$Z^{11}$) and Id'–Ie' (Z=$Z^{12}$) and particular preference is also given to compounds of the formulae If (Z=$Z^9$) and Ig (Z=$Z^{10}$).

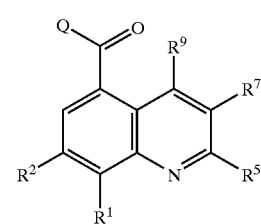

Ia

-continued

Furthermore, preference is given to the compounds Ia, Ib, Ic, Id and Ie.

Preference is also given to the compounds If and Ig where CR³R⁴, CR⁵R⁶, CR⁷R⁸ and/or CR⁹R¹⁰ may not be replaced by C=O or C=NR¹³.

Furthermore, preference is given to the compounds Ig where CR⁵R⁶ is replaced by C=O or C=NR¹³.

Furthermore, preference is given to the compounds Ig where CR³R⁴, CR⁷R⁸ and/or CR⁸R¹⁰ [sic] are replaced by C=O or C=NR¹³.

Very particular preference is given to the compounds Ia1 (=I where R², R¹⁴, R¹⁵, R¹⁶, R¹⁷, R¹⁸ and R¹⁹=H and where the "Q—CO—fragment" is attached in position a, R¹ is attached in position d and Z¹ is attached in positions b and c) listed in Table 1.

TABLE 1

| No. | R¹ | R⁵ | R⁷ | R⁹ |
|---|---|---|---|---|
| Ia1.001 | Br | H | H | H |
| Ia1.002 | Cl | H | H | H |

TABLE 1-continued

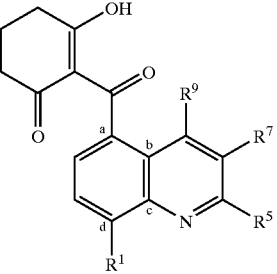

Ia1

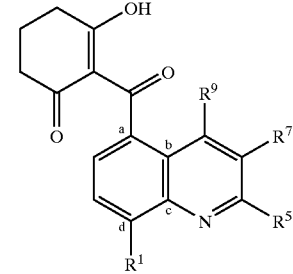

Ia1

| No. | $R^1$ | $R^5$ | $R^7$ | $R^9$ |
|---|---|---|---|---|
| Ia1.003 | SO$_2$CH$_3$ | H | H | H |
| Ia1.004 | CH$_3$ | H | H | H |
| Ia1.005 | OH | H | H | H |
| Ia1.006 | OCH$_3$ | H | H | H |
| Ia1.007 | CF$_3$ | H | H | H |
| Ia1.008 | NO$_2$ | H | H | H |
| Ia1.009 | F | H | H | H |
| Ia1.010 | OCF$_3$ | H | H | H |
| Ia1.011 | C$_6$H$_5$ | H | H | H |
| Ia1.012 | Br | H | CH$_3$ | H |
| Ia1.013 | Cl | H | CH$_3$ | H |
| Ia1.014 | SO$_2$CH$_3$ | H | CH$_3$ | H |
| Ia1.015 | CH$_3$ | H | CH$_3$ | H |
| Ia1.016 | OH | H | CH$_3$ | H |
| Ia1.017 | OCH$_3$ | H | CH$_3$ | H |
| Ia1.018 | CF$_3$ | H | CH$_3$ | H |
| Ia1.019 | NO$_2$ | H | CH$_3$ | H |
| Ia1.020 | F | H | CH$_3$ | H |
| Ia1.021 | OCF$_3$ | H | CH$_3$ | H |
| Ia1.022 | C$_6$H$_5$ | H | CH$_3$ | H |
| Ia1.023 | Br | CH$_3$ | H | H |
| Ia1.024 | Cl | CH$_3$ | H | H |
| Ia1.025 | SO$_2$CH$_3$ | CH$_3$ | H | H |
| Ia1.026 | CH$_3$ | CH$_3$ | H | H |
| Ia1.027 | OH | CH$_3$ | H | H |
| Ia1.028 | OCH$_3$ | CH$_3$ | H | H |
| Ia1.029 | CF$_3$ | CH$_3$ | H | H |
| Ia1.030 | NO$_2$ | CH$_3$ | H | H |
| Ia1.031 | F | CH$_3$ | H | H |
| Ia1.032 | OCF$_3$ | CH$_3$ | H | H |
| Ia1.033 | C$_6$H$_5$ | CH$_3$ | H | H |
| Ia1.034 | Br | H | H | CH$_3$ |
| Ia1.035 | Cl | H | H | CH$_3$ |
| Ia1.036 | SO$_2$CH$_3$ | H | H | CH$_3$ |
| Ia1.037 | CH$_3$ | H | H | CH$_3$ |
| Ia1.038 | OH | H | H | CH$_3$ |
| Ia1.039 | OCH$_3$ | H | H | CH$_3$ |
| Ia1.040 | CF$_3$ | H | H | CH$_3$ |
| Ia1.041 | NO$_2$ | H | H | CH$_3$ |
| Ia1.042 | F | H | H | CH$_3$ |
| Ia1.043 | OCF$_3$ | H | H | CH$_3$ |
| Ia1.044 | C$_6$H$_5$ | H | H | CH$_3$ |
| Ia1.045 | Br | CH$_3$ | CH$_3$ | CH$_3$ |
| Ia1.046 | Cl | CH$_3$ | CH$_3$ | CH$_3$ |
| Ia1.047 | SO$_2$CH$_3$ | CH$_3$ | CH$_3$ | CH$_3$ |
| Ia1.048 | CH$_3$ | CH$_3$ | CH$_3$ | CH$_3$ |
| Ia1.049 | OH | CH$_3$ | CH$_3$ | CH$_3$ |
| Ia1.050 | OCH$_3$ | CH$_3$ | CH$_3$ | CH$_3$ |
| Ia1.051 | CF$_3$ | CH$_3$ | CH$_3$ | CH$_3$ |
| Ia1.052 | NO$_2$ | CH$_3$ | CH$_3$ | CH$_3$ |
| Ia1.053 | F | CH$_3$ | CH$_3$ | CH$_3$ |
| Ia1.054 | OCF$_3$ | CH$_3$ | CH$_3$ | CH$_3$ |
| Ia1.055 | C$_6$H$_5$ | CH$_3$ | CH$_3$ | CH$_3$ |
| Ia1.056 | Br | H | Cl | H |
| Ia1.057 | Cl | H | Cl | H |
| Ia1.058 | SO$_2$CH$_3$ | H | Cl | H |
| Ia1.059 | CH$_3$ | H | Cl | H |
| Ia1.060 | OH | H | Cl | H |
| Ia1.061 | OCH$_3$ | H | Cl | H |
| Ia1.062 | CF$_3$ | H | Cl | H |
| Ia1.063 | NO$_2$ | H | Cl | H |
| Ia1.064 | F | H | Cl | H |
| Ia1.065 | OCF$_3$ | H | Cl | H |
| Ia1.066 | C$_6$H$_5$ | H | Cl | H |
| Ia1.067 | Br | Cl | H | H |
| Ia1.068 | Cl | Cl | H | H |
| Ia1.069 | SO$_2$CH$_3$ | Cl | H | H |
| Ia1.070 | CH$_3$ | Cl | H | H |
| Ia1.071 | OH | Cl | H | H |
| Ia1.072 | OCH$_3$ | Cl | H | H |
| Ia1.073 | CF$_3$ | Cl | H | H |
| Ia1.074 | NO$_2$ | Cl | H | H |
| Ia1.075 | F | Cl | H | H |
| Ia1.076 | OCF$_3$ | Cl | H | H |
| Ia1.077 | C$_6$H$_5$ | Cl | H | H |
| Ia1.078 | Br | H | H | Cl |
| Ia1.079 | Cl | H | H | Cl |
| Ia1.080 | SO$_2$CH$_3$ | H | H | Cl |
| Ia1.081 | CH$_3$ | H | H | Cl |
| Ia1.082 | OH | H | H | Cl |
| Ia1.083 | OCH$_3$ | H | H | Cl |
| Ia1.084 | CF$_3$ | H | H | Cl |
| Ia1.085 | NO$_2$ | H | H | Cl |
| Ia1.086 | F | H | H | Cl |
| Ia1.087 | OCF$_3$ | H | H | Cl |
| Ia1.088 | C$_6$H$_5$ | H | H | Cl |
| Ia1.089 | Br | Cl | Cl | Cl |
| Ia1.090 | Cl | Cl | Cl | Cl |
| Ia1.091 | SO$_2$CH$_3$ | Cl | Cl | Cl |
| Ia1.092 | CH$_3$ | Cl | Cl | Cl |
| Ia1.093 | OH | Cl | Cl | Cl |
| Ia1.094 | OCH$_3$ | Cl | Cl | Cl |
| Ia1.095 | CF$_3$ | Cl | Cl | Cl |
| Ia1.096 | NO$_2$ | Cl | Cl | Cl |
| Ia1.097 | F | Cl | Cl | Cl |
| Ia1.098 | OCF$_3$ | Cl | Cl | Cl |
| Ia1.099 | C$_6$H$_5$ | Cl | Cl | Cl |
| Ia1.100 | Br | C$_6$H$_5$ | H | H |
| Ia1.101 | Cl | C$_6$H$_5$ | H | H |
| Ia1.102 | SO$_2$CH$_3$ | C$_6$H$_5$ | H | H |
| Ia1.103 | CH$_3$ | C$_6$H$_5$ | H | H |
| Ia1.104 | OH | C$_6$H$_5$ | H | H |
| Ia1.105 | OCH$_3$ | C$_6$H$_5$ | H | H |
| Ia1.106 | CF$_3$ | C$_6$H$_5$ | H | H |
| Ia1.107 | NO$_2$ | C$_6$H$_5$ | H | H |
| Ia1.108 | F | C$_6$H$_5$ | H | H |
| Ia1.109 | OCF$_3$ | C$_6$H$_5$ | H | H |
| Ia1.110 | C$_6$H$_5$ | C$_6$H$_5$ | H | H |
| Ia1.111 | Br | CH$_3$ | OH | H |
| Ia1.112 | Cl | CH$_3$ | OH | H |
| Ia1.113 | SO$_2$CH$_3$ | CH$_3$ | OH | H |
| Ia1.114 | CH$_3$ | CH$_3$ | OH | H |
| Ia1.115 | OH | CH$_3$ | OH | H |
| Ia1.116 | OCH$_3$ | CH$_3$ | OH | H |
| Ia1.117 | CF$_3$ | CH$_3$ | OH | H |
| Ia1.118 | NO$_2$ | CH$_3$ | OH | H |
| Ia1.119 | F | CH$_3$ | OH | H |
| Ia1.120 | OCF$_3$ | CH$_3$ | OH | H |
| Ia1.121 | C$_6$H$_5$ | CH$_3$ | OH | H |
| Ia1.122 | Br | CF$_3$ | H | H |
| Ia1.123 | Cl | CF$_3$ | H | H |
| Ia1.124 | SO$_2$CH$_3$ | CF$_3$ | H | H |
| Ia1.125 | CH$_3$ | CF$_3$ | H | H |
| Ia1.126 | OH | CF$_3$ | H | H |

TABLE 1-continued

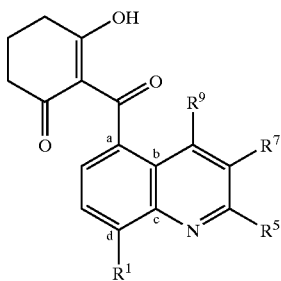

Ia1

| No. | R¹ | R⁵ | R⁷ | R⁹ |
|---|---|---|---|---|
| Ia1.127 | OCH₃ | CF₃ | H | H |
| Ia1.128 | CF₃ | CF₃ | H | H |
| Ia1.129 | NO₂ | CF₃ | H | H |
| Ia1.130 | F | CF₃ | H | H |
| Ia1.131 | OCF₃ | CF₃ | H | H |
| Ia1.132 | C₆H₅ | CF₃ | H | H |
| Ia1.133 | Br | CH₃ | H | OH |
| Ia1.134 | Cl | CH₃ | H | OH |
| Ia1.135 | SO₂CH₃ | CH₃ | H | OH |
| Ia1.136 | CH₃ | CH₃ | H | OH |
| Ia1.137 | OH | CH₃ | H | OH |
| Ia1.138 | OCH₃ | CH₃ | H | OH |
| Ia1.139 | CF₃ | CH₃ | H | OH |
| Ia1.140 | NO₂ | CH₃ | H | OH |
| Ia1.141 | F | CH₃ | H | OH |
| Ia1.142 | OCF₃ | CH₃ | H | OH |
| Ia1.143 | C₆H₅ | CH₃ | H | OH |
| Ia1.144 | Br | H | H | OCH₃ |
| Ia1.145 | Cl | H | H | OCH₃ |
| Ia1.146 | SO₂CH₃ | H | H | OCH₃ |
| Ia1.147 | CH₃ | H | H | OCH₃ |
| Ia1.148 | OH | H | H | OCH₃ |
| Ia1.149 | OCH₃ | H | H | OCH₃ |
| Ia1.150 | CF₃ | H | H | OCH₃ |
| Ia1.151 | NO₂ | H | H | OCH₃ |
| Ia1.152 | F | H | H | OCH₃ |
| Ia1.153 | H | H | H | OCH₃ |
| Ia1.154 | OCF₃ | H | H | OCH₃ |
| Ia1.155 | C₆H₅ | H | H | OCH₃ |
| Ia1.156 | Br | Cl | Cl | CH₃ |
| Ia1.157 | Cl | Cl | Cl | CH₃ |
| Ia1.158 | SO₂CH₃ | Cl | Cl | CH₃ |
| Ia1.159 | CH₃ | Cl | Cl | CH₃ |
| Ia1.160 | OH | Cl | Cl | CH₃ |
| Ia1.161 | OCH₃ | Cl | Cl | CH₃ |
| Ia1.162 | CF₃ | Cl | Cl | CH₃ |
| Ia1.163 | NO₂ | Cl | Cl | CH₃ |
| Ia1.164 | F | Cl | Cl | CH₃ |
| Ia1.165 | OCF₃ | Cl | Cl | CH₃ |
| Ia1.166 | C₆H₅ | Cl | Cl | CH₃ |
| Ia1.167 | Br | CF₃ | H | Br |
| Ia1.168 | Cl | CF₃ | H | Br |
| Ia1.169 | SO₂CH₃ | CF₃ | H | Br |
| Ia1.170 | CH₃ | CF₃ | H | Br |
| Ia1.171 | OH | CF₃ | H | Br |
| Ia1.172 | OCH₃ | CF₃ | H | Br |
| Ia1.173 | CF₃ | CF₃ | H | Br |
| Ia1.174 | NO₂ | CF₃ | H | Br |
| Ia1.175 | F | CF₃ | H | Br |
| Ia1.176 | H | CF₃ | H | Br |
| Ia1.177 | OCF₃ | CF₃ | H | Br |
| Ia1.178 | C₆H₅ | CF₃ | H | Br |
| Ia1.179 | Br | OH | CN | H |
| Ia1.180 | Cl | OH | CN | H |
| Ia1.181 | SO₂CH₃ | OH | CN | H |
| Ia1.182 | CH₃ | OH | CN | H |
| Ia1.183 | OH | OH | CN | H |
| Ia1.184 | OCH₃ | OH | CN | H |
| Ia1.185 | CF₃ | OH | CN | H |
| Ia1.186 | NO₂ | OH | CN | H |
| Ia1.187 | F | OH | CN | H |
| Ia1.188 | OCF₃ | OH | CN | H |
| Ia1.189 | C₆H₅ | OH | CN | H |
| Ia1.190 | Br | H | CF₃ | H |
| Ia1.191 | Cl | H | CF₃ | H |
| Ia1.192 | SO₂CH₃ | H | CF₃ | H |
| Ia1.193 | CH₃ | H | CF₃ | H |
| Ia1.194 | OH | H | CF₃ | H |
| Ia1.195 | OCH₃ | H | CF₃ | H |
| Ia1.196 | CF₃ | H | CF₃ | H |
| Ia1.197 | NO₂ | H | CF₃ | H |
| Ia1.198 | F | H | CF₃ | H |
| Ia1.199 | OCF₃ | H | CF₃ | H |
| Ia1.200 | C₆H₅ | H | CF₃ | H |
| Ia1.201 | Br | H | H | NO₂ |
| Ia1.202 | Cl | H | H | NO₂ |
| Ia1.203 | SO₂CH₃ | H | H | NO₂ |
| Ia1.204 | CH₃ | H | H | NO₂ |
| Ia1.205 | OH | H | H | NO₂ |
| Ia1.206 | OCH₃ | H | H | NO₂ |
| Ia1.207 | CF₃ | H | H | NO₂ |
| Ia1.208 | NO₂ | H | H | NO₂ |
| Ia1.209 | F | H | H | NO₂ |
| Ia1.210 | OCF₃ | H | H | NO₂ |
| Ia1.211 | C₆H₅ | H | H | NO₂ |

Furthermore, very particular preference is given to the following hetaroyl derivatives of the formula I:

the compounds Ia2.001–Ia2.211, which differ from the corresponding compounds Ia1.001–Ia1.211 in that $R^{16}$ is methyl:

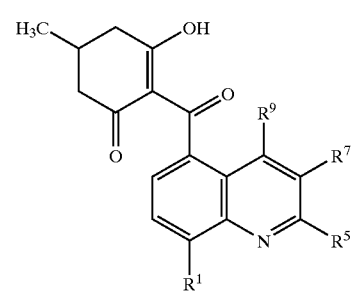

Ia2 the compounds Ia3.001–Ia3.211, which differ from the corresponding compounds Ia1.001–Ia1.211 in that $R^{16}$ and $R^{17}$ are each methyl:

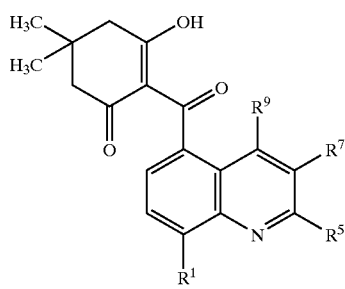

Ia3 the compounds Ia4.001–Ia4.211, which differ from the corresponding compounds Ia1.001–Ia1.211 in that $R^{18}$ and $R^{19}$ are each methyl:

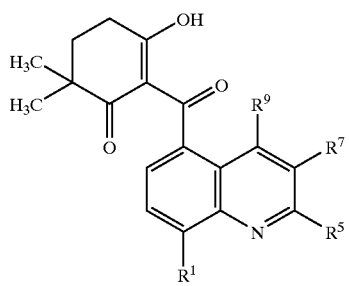

Ia4 the compounds Ia5.001–Ia5.211, which differ from the corresponding compounds Ia1.001–Ia1.211 in that the —$CR^{16}R^{17}$— unit is replaced by C=O:

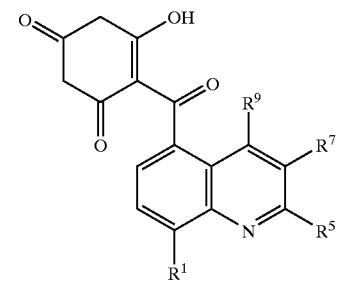

Ia5 the compounds Ia6.001–Ia6.211, which differ from the corresponding compounds Ia1.001–Ia1.211 in that $R^{14}$, $R^{18}$ and $R^{19}$ are each methyl and in that the —$CR^{16}R^{17}$— unit is replaced by C=O:

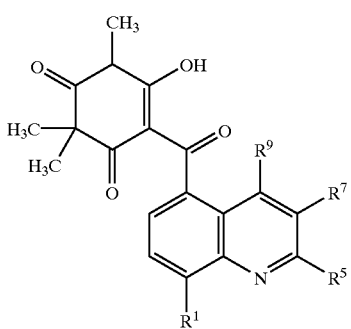

Ia6 the compounds Ia7.001–Ia7.211, which differ from the corresponding compounds Ia1.001–Ia1.211 in that $R^{14}_{1}$ $R^{15}$, $R^{18}$ and $R^{19}$ are each methyl and in that the —$CR^{16}R^{17}$— unit is replaced by C=O:

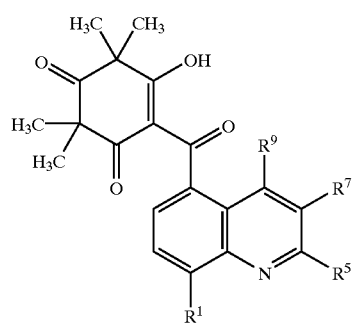

Ia7 the compounds Ia'1.001–Ia'.1.211, which differ from the corresponding compounds Ia1.001–Ia1.211 in that they are the N-oxides (Z=$Z^{11}$):

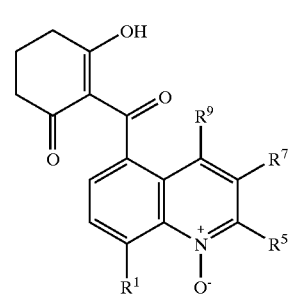

Ia'1 the compounds Ia'2.001–Ia'2.211, which differ from the corresponding compounds Ia1.001–Ia1.211 in that $R^{16}$ is methyl and in that they are the N-oxides (Z=$Z^{11}$)

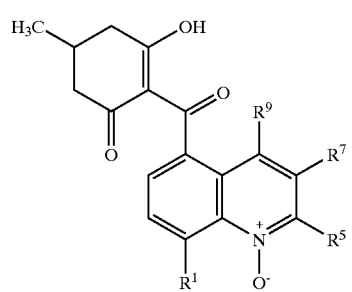

Ia'2 the compounds Ia'3.001–Ia'3.211, which differ from the corresponding compounds Ia1.001–Ia1.211 in that $R^{16}$ and $R^{17}$ are each methyl and in that they are the N-oxides (Z=$Z^{11}$):

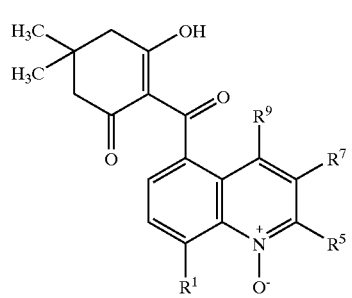

Ia'3 the compounds Ia'4.001–Ia'4.211, which differ from the corresponding compounds Ia1.001–Ia1.211 in that $R^{18}$ and $R^{19}$ are each methyl and in that they are the N-oxides (Z=$Z^{11}$):

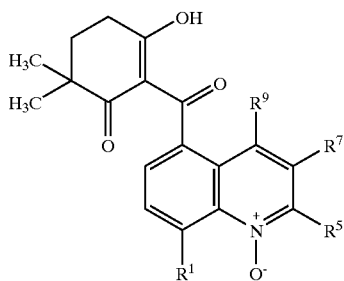

Ia'4 the compounds Ia,5.001–Ia'5.211, which differ from the corresponding compounds Ia1.001–Ia1.211 in that the —CR$^{16}$R$^{17}$— unit is replaced by C=O and in that they are the N-oxides (Z=Z$^{11}$):

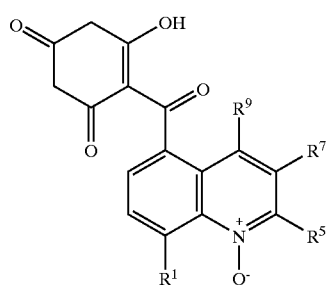

Ia'5 the compounds Ia'6.001–Ia'6.211, which differ from the corresponding compounds Ia1.001–Ia1.211 in that R$^{14}$, R$^{18}$ and R$^{19}$ are each methyl, the —CR$^{16}$R$^{17}$— unit is replaced by C=O and in that they are the N-oxides (Z=Z$^{11}$):

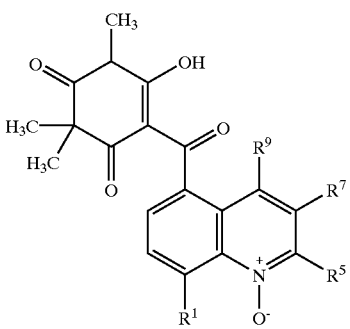

Ia'6 the compounds Ia'7.001–Ia'7.211, which differ from the corresponding compounds Ia1.001–Ia1.211 in that R$^{14}$, R$^{15}$, R$^{18}$ and R$^{19}$ are each methyl, the —CR$^{16}$R$^{17}$— unit is replaced by C=O and in that they are the N-oxides (Z=Z$^{11}$):

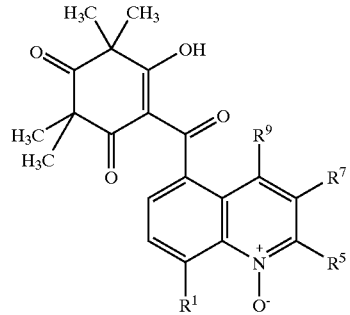

Ia'7

Likewise, very particular preference is given to the compounds Ib1 (=I where R$^{14}$, R$^{15}$, R$^{16}$, R$^{17}$, R$^{18}$ and R$^{19}$ =H and where the "Q—CO— fragment" is attached in position e, R$^{1}$ is attached in position d, R$^{2}$ is attached in position a and Z$^{1}$ is attached in positions b and c) listed in Table 2 below.

TABLE 2

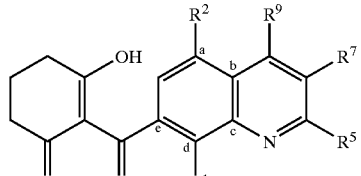

Ib1

| No. | R$^1$ | R$^2$ | R$^5$ | R$^7$ | R$^9$ |
|---|---|---|---|---|---|
| Ib1.01 | CH$_3$ | H | H | H | H |
| Ib1.02 | CH$_3$ | H | H | H | CH$_3$ |
| Ib1.03 | CH$_3$ | H | H | CH$_3$ | H |
| Ib1.04 | CH$_3$ | H | CH$_3$ | H | H |
| Ib1.05 | CH$_3$ | CH$_3$ | H | H | H |
| Ib1.06 | CH$_3$ | H | H | H | Cl |
| Ib1.07 | CH$_3$ | H | H | Cl | H |
| Ib1.08 | CH$_3$ | H | Cl | H | H |
| Ib1.09 | CH$_3$ | Cl | H | H | H |
| Ib1.10 | CH$_3$ | H | H | H | CF$_3$ |
| Ib1.11 | CH$_3$ | H | H | CF$_3$ | H |
| Ib1.12 | CH$_3$ | H | CF$_3$ | H | H |
| Ib1.13 | Cl | H | H | H | H |
| Ib1.14 | Cl | H | H | H | CH$_3$ |
| Ib1.15 | Cl | H | H | CH$_3$ | H |
| Ib1.16 | Cl | H | CH$_3$ | H | H |
| Ib1.17 | Cl | H | H | H | Cl |
| Ib1.18 | Cl | H | H | Cl | H |
| Ib1.19 | Cl | H | Cl | H | H |
| Ib1.20 | Cl | H | Cl | Cl | Cl |
| Ib1.21 | CH$_3$ | H | CH$_3$ | CH$_3$ | CH$_3$ |

Furthermore, very particular preference is given to the following hetaroyl derivatives of the formula I:

the compounds Ib2.01–Ib2.21, which differ from the corresponding compounds Ib1.01–Ib1.21 in that R$^{16}$ is methyl:

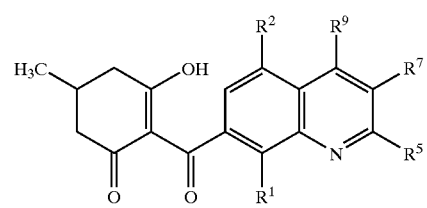

Ib2 the compounds Ib3.01–Ib3.21, which differ from the corresponding compounds Ib1.01–Ib1.21 in that R$^{16}$ and R$^{17}$ are each methyl:

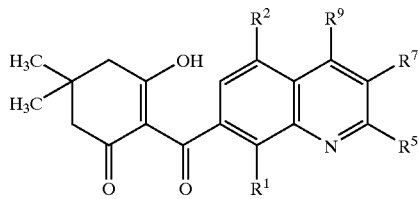

Ib3 the compounds Ib4.01–Ib4.21, which differ from the corresponding compounds Ib1.01–Ib1.21 in that R$^{18}$ and R$^{19}$ are each methyl:

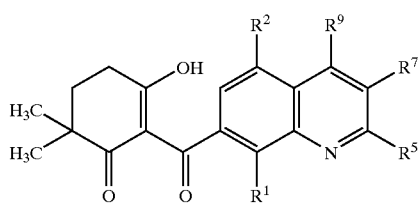

Ib4 the compounds Ib5.01–Ib5.21, which differ from the corresponding compounds Ib1.01–Ib1.21 in that the —CR$^{16}$R$^{17}$— unit is replaced by C=O:

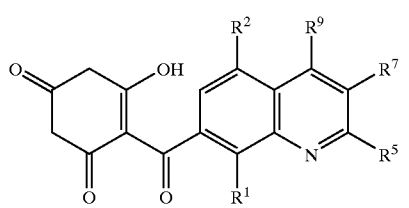

Ib5 the compounds Ib6.01–Ib6.21, which differ from the corresponding compounds Ib1.01–Ib1.21 in that R$^{14}$, R$^{18}$ and R$^{19}$ are each methyl and in that the —CR$^{16}$R$^{17}$— unit is replaced by C=O:

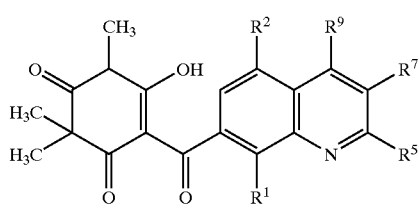

Ib6 the compounds Ib7.01–Ib7.21, which differ from the corresponding compounds Ib1.01–Ib1.21 in that R$^{14}$, R$^{15}$, R$^{18}$ and R$^{19}$ are each methyl and in that the —CR$^{16}$R$^{17}$— unit is replaced by C=O:

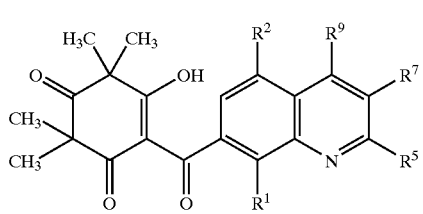

Ib7

Likewise, very particular preference is given to the compounds Ic1 (=I where R$^2$, R$^{14}$, R$^{15}$, R$^{16}$, R$^{17}$, R$^{18}$ and R$^{19}$=H and where the "Q—CO— fragment" is attached in position d, R$^1$ is attached in position a and Z$^1$ is attached in positions b and c) listed in Table 3 below:

TABLE 3

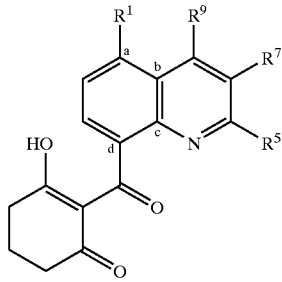

Ic1

| No. | R$^1$ | R$^5$ | R$^7$ | R$^9$ |
|---|---|---|---|---|
| Ic1.01 | Br | CH$_3$ | H | H |
| Ic1.02 | Cl | CH$_3$ | H | H |
| Ic1.03 | SO$_2$CH$_3$ | CH$_3$ | H | H |
| Ic1.04 | CH$_3$ | CH$_3$ | H | H |
| Ic1.05 | OH | CH$_3$ | H | H |
| Ic1.06 | OCH$_3$ | CH$_3$ | H | H |
| Ic1.07 | CF$_3$ | CH$_3$ | H | H |
| Ic1.08 | NO$_2$ | CH$_3$ | H | H |
| Ic1.09 | F | CH$_3$ | H | H |
| Ic1.10 | OCF$_3$ | CH$_3$ | H | H |
| Ic1.11 | C$_6$H$_5$ | CH$_3$ | H | H |
| Ic1.12 | Br | CF$_3$ | H | H |
| Ic1.13 | Cl | CF$_3$ | H | H |
| Ic1.14 | SO$_2$CH$_3$ | CF$_3$ | H | H |
| Ic1.15 | CH$_3$ | CF$_3$ | H | H |
| Ic1.16 | OH | CF$_3$ | H | H |
| Ic1.17 | OCH$_3$ | CF$_3$ | H | H |
| Ic1.18 | CF$_3$ | CF$_3$ | H | H |
| Ic1.19 | NO$_2$ | CF$_3$ | H | H |
| Ic1.20 | F | CF$_3$ | H | H |
| Ic1.21 | OCF$_3$ | CF$_3$ | H | H |
| Ic1.22 | C$_6$H$_5$ | CF$_3$ | H | H |
| Ic1.23 | Br | H | H | H |
| Ic1.24 | Cl | H | H | H |
| Ic1.25 | SO$_2$CH$_3$ | H | H | H |
| Ic1.26 | CH$_3$ | H | H | H |
| Ic1.27 | OH | H | H | H |
| Ic1.28 | OCH$_3$ | H | H | H |
| Ic1.29 | CF$_3$ | H | H | H |
| Ic1.30 | NO$_2$ | H | H | H |
| Ic1.31 | F | H | H | H |
| Ic1.32 | OCF$_3$ | H | H | H |
| Ic1.33 | C$_6$H$_5$ | H | H | H |
| Ic1.34 | Br | Cl | H | H |
| Ic1.35 | Cl | Cl | H | H |
| Ic1.36 | SO$_2$CH$_3$ | Cl | H | H |
| Ic1.37 | CH$_3$ | Cl | H | H |
| Ic1.38 | OH | Cl | H | H |
| Ic1.39 | OCH$_3$ | Cl | H | H |
| Ic1.40 | CF$_3$ | Cl | H | H |
| Ic1.41 | NO$_2$ | Cl | H | H |
| Ic1.42 | F | Cl | H | H |
| Ic1.43 | OCF$_3$ | Cl | H | H |
| Ic1.44 | C$_6$H$_5$ | Cl | H | H |

Furthermore, very particular preference is given to the following hetaroyl derivatives of the formula I:

the compounds Ic2.01–Ic2.44, which differ from the compounds Ic1.01–Ic1.44 in that R$^{16}$ is methyl:

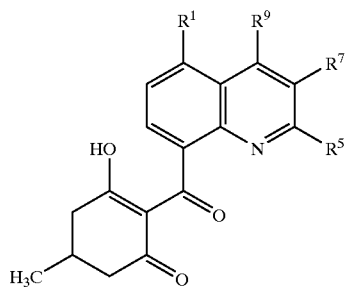

Ic2 the compounds Ic3.01–Ic3.44, which differ from the compounds Ic1.01–Ic1.44 in that $R^{16}$ and $R^{17}$ are each methyl:

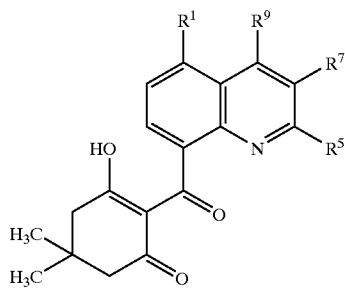

Ic3 the compounds Ic4.01–Ic4.44, which differ from the compounds Ic1.01–Ic1.44 in that $R^{18}$ and $R^{19}$ are each methyl:

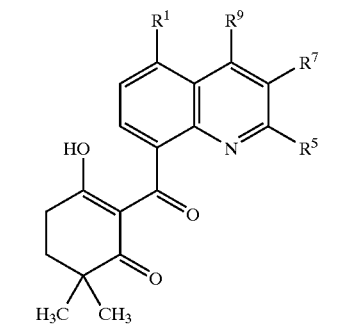

Ic4 the compounds Ic5.01–Ic5.44, which differ from the corresponding compounds Ic1.01–Ic1.44 in that the —$CR^{16}R^{17}$— unit is replaced by C=O:

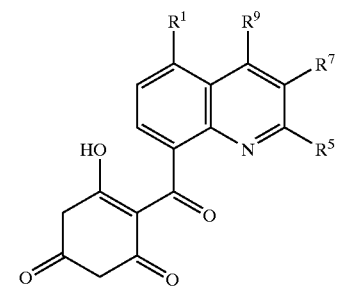

Ic5 the compounds Ic6.01–Ic6.44, which differ from the corresponding compounds Ic1.01–Ic1.44 in that $R^{14}$, $R^{18}$ and $R^{19}$ are each methyl and in that the —$CR^{16}R^{17}$— unit is replaced by C=O:

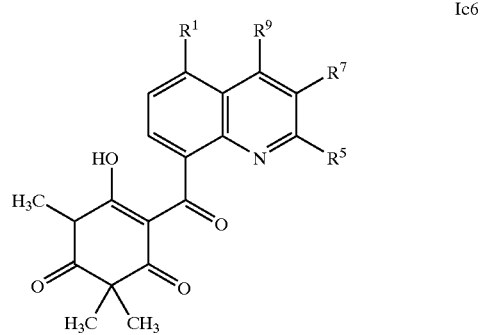

Ic6 the compounds Ic7.01–Ic7.44, which differ from the corresponding compounds Ic1.01–Ic1.44 in that $R^{14}$, $R^{15}$, $R^{18}$ and $R^{19}$ are each methyl and in that the —$CR^{16}R^{17}$— unit is replaced by C=O:

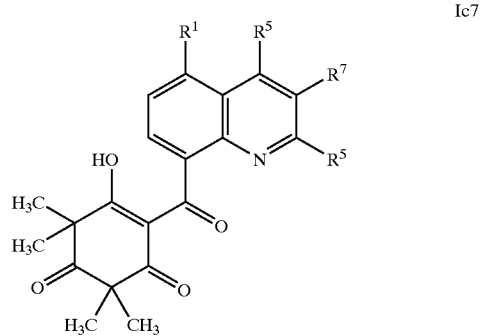

Ic7

In addition very particular preference is given to the compounds Id1 (=I where $R^2$, $R^{14}$, $R^{15}$, $R^{16}$, $R^{17}$, $R^{18}$ and $R^{19}$=H and where the "Q—CO— fragment" is attached in position a, $R^1$ is attached in position d and $Z^2$ is attached in positions b and c) listed in Table 4 below:

TABLE 4

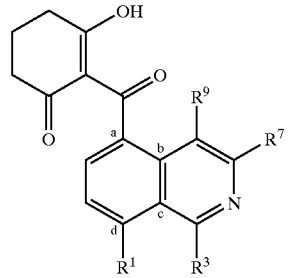

Id1

| No. | $R^1$ | $R^3$ | $R^7$ | $R^9$ |
|---|---|---|---|---|
| Id1.01 | Br | H | H | H |
| Id1.02 | Cl | H | H | H |
| Id1.03 | $SO_2CH_3$ | H | H | H |
| Id1.04 | $CH_3$ | H | H | H |
| Id1.05 | OH | H | H | H |
| Id1.06 | $OCH_3$ | H | H | H |
| Id1.07 | $CF_3$ | H | H | H |
| Id1.08 | $NO_2$ | H | H | H |

TABLE 4-continued

Id1

| No. | $R^1$ | $R^3$ | $R^7$ | $R^9$ |
|---|---|---|---|---|
| Id1.09 | F | H | H | H |
| Id1.10 | $OCF_3$ | H | H | H |
| Id1.11 | Br | $CH_3$ | H | H |
| Id1.12 | Cl | $CH_3$ | H | H |
| Id1.13 | $SO_2CH_3$ | $CH_3$ | H | H |
| Id1.14 | $CH_3$ | $CH_3$ | H | H |
| Id1.15 | OH | $CH_3$ | H | H |
| Id1.16 | $OCH_3$ | $CH_3$ | H | H |
| Id1.17 | $CF_3$ | $CH_3$ | H | H |
| Id1.18 | $NO_2$ | $CH_3$ | H | H |
| Id1.19 | F | $CH_3$ | H | H |
| Id1.20 | H | $CH_3$ | H | H |
| Id1.21 | $OCF_3$ | $CH_3$ | H | H |
| Id1.22 | Br | $CH_3$ | $CH_3$ | H |
| Id1.23 | Cl | $CH_3$ | $CH_3$ | H |
| Id1.24 | $SO_2CH_3$ | $CH_3$ | $CH_3$ | H |
| Id1.25 | $CH_3$ | $CH_3$ | $CH_3$ | H |
| Id1.26 | OH | $CH_3$ | $CH_3$ | H |
| Id1.27 | $OCH_3$ | $CH_3$ | $CH_3$ | H |
| Id1.28 | $CF_3$ | $CH_3$ | $CH_3$ | H |
| Id1.29 | $NO_2$ | $CH_3$ | $CH_3$ | H |
| Id1.30 | F | $CH_3$ | $CH_3$ | H |
| Id1.31 | $OCF_3$ | $CH_3$ | $CH_3$ | H |
| Id1.32 | Br | Cl | Cl | Cl |
| Id1.33 | Cl | Cl | Cl | Cl |
| Id1.34 | $SO_2CH_3$ | Cl | Cl | Cl |
| Id1.35 | $CH_3$ | Cl | Cl | Cl |
| Id1.36 | OH | Cl | Cl | Cl |
| Id1.37 | $OCH_3$ | Cl | Cl | Cl |
| Id1.38 | $CF_3$ | Cl | Cl | Cl |
| Id1.39 | $NO_2$ | Cl | Cl | Cl |
| Id1.40 | F | Cl | Cl | Cl |
| Id1.41 | $OCF_3$ | Cl | Cl | Cl |
| Id1.42 | Br | $OCH_3$ | Cl | H |
| Id1.43 | Cl | $OCH_3$ | Cl | H |
| Id1.44 | $SO_2CH_3$ | $OCH_3$ | Cl | H |
| Id1.45 | $CH_3$ | $OCH_3$ | Cl | H |
| Id1.46 | OH | $OCH_3$ | Cl | H |
| Id1.47 | $OCH_3$ | $OCH_3$ | Cl | H |
| Id1.48 | $CF_3$ | $OCH_3$ | Cl | H |
| Id1.49 | $NO_2$ | $OCH_3$ | Cl | H |
| Id1.50 | F | $OCH_3$ | Cl | H |
| Id1.51 | $OCF_3$ | $OCH_3$ | Cl | H |
| Id1.52 | Br | H | $OCH_3$ | H |
| Id1.53 | Cl | H | $OCH_3$ | H |
| Id1.54 | $SO_2CH_3$ | H | $OCH_3$ | H |
| Id1.55 | $CH_3$ | H | $OCH_3$ | H |
| Id1.56 | OH | H | $OCH_3$ | H |
| Id1.57 | $OCH_3$ | H | $OCH_3$ | H |
| Id1.58 | $CF_3$ | H | $OCH_3$ | H |
| Id1.59 | $NO_2$ | H | $OCH_3$ | H |
| Id1.60 | F | H | $OCH_3$ | H |
| Id1.61 | $OCF_3$ | H | $OCH_3$ | H |
| Id1.62 | Br | $CH_3$ | $CH_3$ | $CH_3$ |
| Id1.63 | Cl | $CH_3$ | $CH_3$ | $CH_3$ |
| Id1.64 | $SO_2CH_3$ | $CH_3$ | $CH_3$ | $CH_3$ |
| Id1.65 | $CH_3$ | $CH_3$ | $CH_3$ | $CH_3$ |
| Id1.66 | OH | $CH_3$ | $CH_3$ | $CH_3$ |
| Id1.67 | $OCH_3$ | $CH_3$ | $CH_3$ | $CH_3$ |
| Id1.68 | $CF_3$ | $CH_3$ | $CH_3$ | $CH_3$ |
| Id1.69 | $NO_2$ | $CH_3$ | $CH_3$ | $CH_3$ |
| Id1.70 | F | $CH_3$ | $CH_3$ | $CH_3$ |
| Id1.71 | $OCF_3$ | $CH_3$ | $CH_3$ | $CH_3$ |
| Id1.72 | Br | Cl | H | H |
| Id1.73 | Cl | Cl | H | H |
| Id1.74 | $SO_2CH_3$ | Cl | H | H |
| Id1.75 | $CH_3$ | Cl | H | H |
| Id1.76 | OH | Cl | H | H |
| Id1.77 | $OCH_3$ | Cl | H | H |
| Id1.78 | $CF_3$ | Cl | H | H |
| Id1.79 | $NO_2$ | Cl | H | H |
| Id1.80 | F | Cl | H | H |
| Id1.81 | $OCF_3$ | Cl | H | H |
| Id1.82 | Br | Cl | Cl | H |
| Id1.83 | Cl | Cl | Cl | H |
| Id1.84 | $SO_2CH_3$ | Cl | Cl | H |
| Id1.85 | $CH_3$ | Cl | Cl | H |
| Id1.86 | OH | Cl | Cl | H |
| Id1.87 | $OCH_3$ | Cl | Cl | H |
| Id1.88 | $CF_3$ | Cl | Cl | H |
| Id1.89 | $NO_2$ | Cl | Cl | H |
| Id1.90 | F | Cl | Cl | H |
| Id1.91 | $OCF_3$ | Cl | Cl | H |

Furthermore, very particular preference is given to the following hetaroyl derivatives of the formula I:

the compounds Id2.01–Id2.91, which differ from the compounds Id1.01–Id1.91 in that $R^{16}$ is methyl:

Id2 the compounds Id3.01–Id3.91, which differ from the compounds Id1.01–Id1.91 in that $R^{16}$ and $R^{17}$ are each methyl:

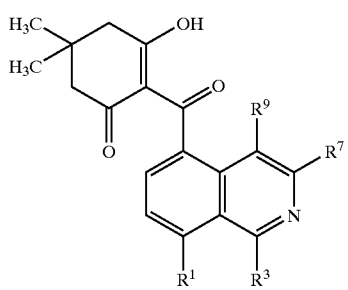

Id3 the compounds Id4.01–Id4.91, which differ from the compounds Id1.01–Id1.91 in that $R^{18}$ and $R^{19}$ are each methyl:

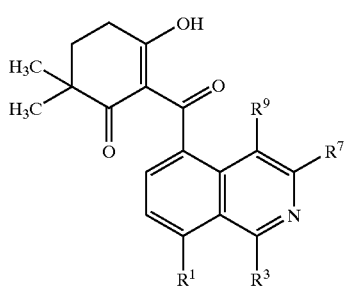

Id4 the compounds Id5.01–Id5.91, which differ from the corresponding compounds Id1.01–Id1.91 in that the —$CR^{16}R^{17}$— unit is replaced by C=O:

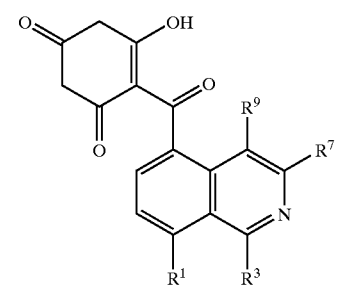

Id5 the compounds Id6.01–Id6.91, which differ from the corresponding compounds Id1.01–Id1.91 in that $R^{14}$, $R^{18}$ and $R^{19}$ are each methyl and in that the —$CR^{16}R^{17}$— unit is replaced by C=O:

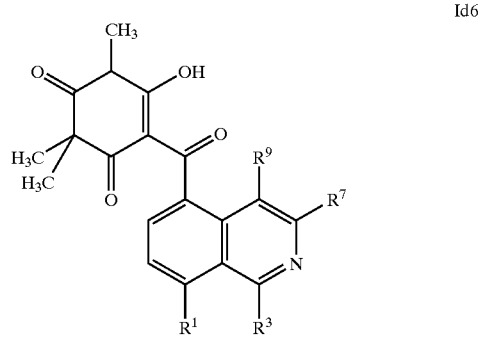

Id6 the compounds Id7.01–Id7.91, which differ from the corresponding compounds Id1.01–Id1.91 in that $R^{14}$, $R^{15}$, $R^{18}$ and $R^{19}$ are each methyl and the —$CR^{16}R^{17}$— unit is replaced by C=O:

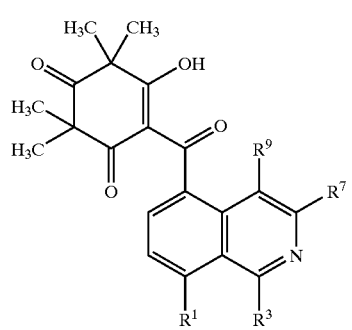

Id7

The hetaroyl derivatives of the formula I can be obtained by different routes, for example by the following process:

Reaction of cyclohexanediones of the formula II with an activated carboxylic acid IIIa or a carboxylic acid IIIb which is preferably activated in situ to give the acylation product, and subsequent rearrangement.

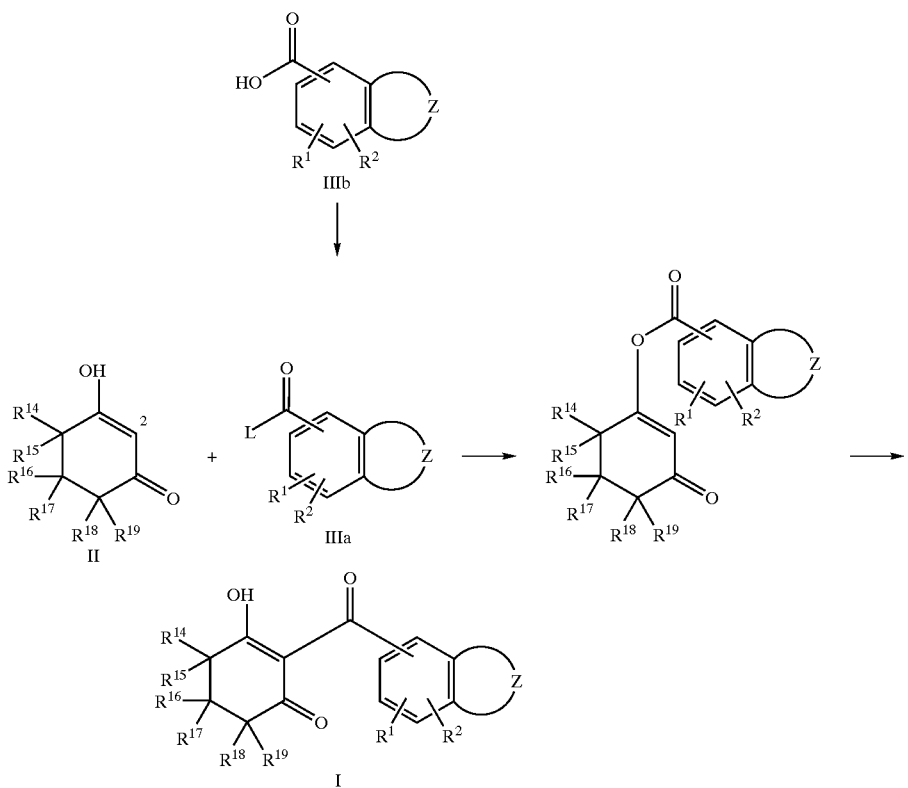

L represents a nucleophilically replaceable leaving group, such as halogen, for example bromine or chlorine, heterocyclyl, for example imidazolyl or pyridyl, or carboxylate, for example acetate, trifluoroacetate, etc.

The activated hetaroylcarboxylic acid can be employed directly, as in the case of the hetaroyl halides, or formed in situ, for example by using dicyclohexylcarbodiimide, triphenylphosphine/azodicarboxylic ester, 2-pyridine [sic] disulfite/triphenylphosphine, carbonyldiimidazole, etc.

It may be advantageous to carry out the acylation reaction in the presence of a base. It is advantageous to employ the reactants and the auxiliary base in equimolar amounts. In certain cases, a small excess of the auxiliary base, for example 1.2 to 1.5 molar equivalents based on II, may be advantageous.

Suitable auxiliary bases include tertiary alkylamines, pyridine and alkali metal carbonates. Suitable solvents are, for example, chlorinated hydrocarbons, such as methylene chloride and 1,2-dichloroethane, aromatic hydrocarbons, such as toluene, xylene and chlorobenzene, ethers,, such as diethyl ether, methyl tert-butyl ether, tetrahydrofuran and dioxane, polar aprotic solvents, such as acetonitrile, dimethylformamide or dimethyl sulfoxide or esters, such as ethyl acetate, or mixtures thereof.

If carboxylic acid halides are employed as activated carboxylic acid component, it may be advantageous to cool the reaction mixture to 0–10° C. when adding this reactant. Stirring is then continued at 20–100° C., preferably at 25–50° C., until the reaction has ended. Work-up is carried out in a conventional manner; for instance, the reaction mixture is poured into water and the product of value is extracted. Suitable solvents for this purpose are in particular methylene chloride, diethyl ether and ethyl acetate. After drying of the organic phase and removal of the solvent, the crude enol ester can be used for the rearrangement without any further purification.

The rearrangement of the enol esters to give the compounds of the formula I is advantageously carried out at from to 20–40° C. in a solvent and in the presence of an auxiliary base using a cyano compound as catalyst.

Suitable solvents are, for example, acetonitrile, methylene chloride, 1,2-dichloroethane, ethyl acetate, toluene, or mixtures thereof. The preferred solvent is acetonitrile.

Suitable auxiliary bases are tertiary amines, such as triethylamine, pyridine or alkali metal carbonates, such as sodium carbonate and potassium carbonate, which are preferably employed in equimolar amounts or up to a fourfold excess, based on the enol ester. Preference is given to using triethylamine, preferably in double the equimolar amount based on the enol ester.

Suitable "rearrangement catalysts" include inorganic cyanides, such as sodium cyanide and potassium cyanide, and organic cyano compounds, such as acetone cyanohydrin and trimethylsilyl cyanide. They are employed in an amount of from 1 to 50 mol percent, based on the enol ester. Preference is given to using acetone cyanohydrin or trimethylsilyl cyanide, for example in an amount of from to 15, preferably 10, mol percent based on the enol ester.

Work-up can be carried out in a known manner. The reaction mixture is acidified, for example with dilute mineral acid, such as 5% strength hydrochloric acid or sulfuric acid, and extracted with an organic solvent, for example methylene chloride or ethyl acetate. The organic extract can be extracted with 5–10% strength alkali metal carbonate solution, for example with sodium carbonate solution or potassium carbonate solution. The aqueous phase is acidified and the resulting precipitate is filtered off with suction and/or extracted with methylene chloride or ethyl acetate, dried and concentrated. (Examples of the preparation of enol esters of cyclohexane-1,3-diones and of the. cyanide-catalyzed rearrangement of the enol esters are described, for example, in EP-A 186 118 and U.S. Pat. No. 4 780 127).

Those cyclohexane-1,3-diones of the formula II used as starting materials which are not already known can be obtained in a conventional manner (for example EP-A 71 707, EP-A 142 741, EP-A 243 313, U.S. Pat. No. 4 249 937; WO 92/13821).

The carboxylic acid halides of the formula IIIa (where L=Br, Cl) which are not already known can be obtained in a conventional manner by reacting the carboxylic acids of the formula IIIb with halogenating reagents such as thionyl chloride, thionyl bromide, phosgene, diphosgene, triphosgene, oxalyl chloride and oxalyl bromide.

Those carboxylic acids of the formula IIIb which are not already known can be obtained in a conventional manner (The Chemistry of Heterocyclic Compounds, Vol. 32, "Quinolines, Part I, II and III", Editor E. Taylor, publisher Wiley & Sons; The Chemistry of Heterocyclic Compounds, Vol. 38, "Isoquinolines, Part I and II", Editor A. Weissemberger and E. Taylor, publisher Wiley & Sons; T. Eicher, S. Hauptmann, "Chemie der Heterocyclen", Thieme Verlag 1994).

For example, unsubstituted or substituted aminobenzoic acids can be reacted with glycerol, unsubstituted or substituted glycerol derivatives or α,β-unsaturated carbonyl compounds by the method of Skraup to give the corresponding quinolinecarboxylic acids (cf. EP-A 294 685, DE-A 33 26 225) (Scheme 1)

(Scheme 1)

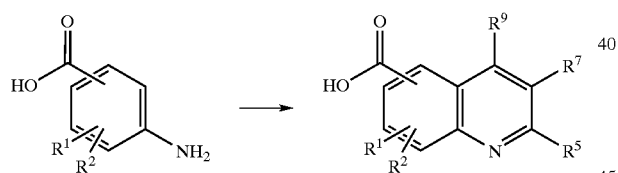

Likewise, it is possible to react unsubstituted or substituted anilines with glycerol, unsubstituted or substituted glycerol derivatives or α,β-unsaturated carbonyl compounds. After halogenation and exchange of the halogen function by cyanide (for example using copper(I) cyanide), the nitrile is hydrolyzed to give the corresponding quinolinecarboxylic acid (cf. Khim. Greterotsikl. Soedin 3 1980, 366 (=CA 93, 71504)). (Scheme 2)

Scheme 2

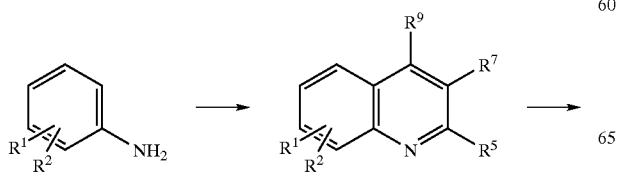

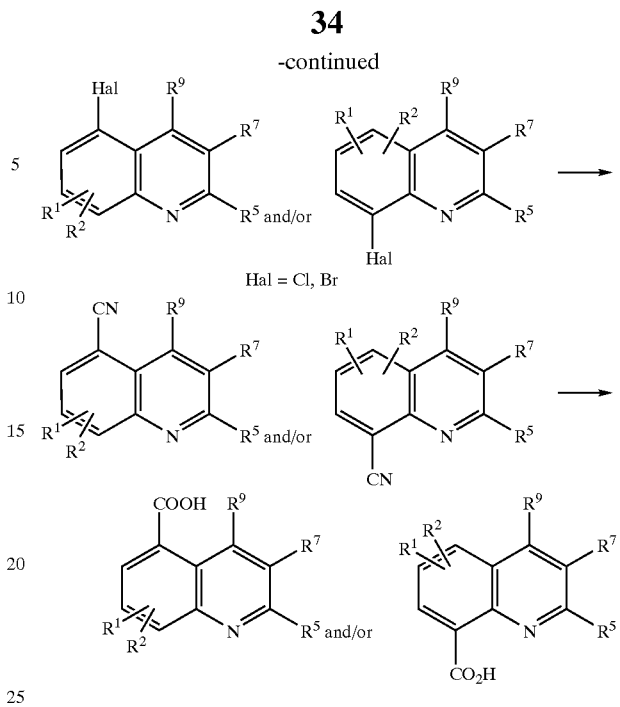

Anilines which are not already known from the literature can be obtained by reducing the corresponding nitrobenzenes. Suitable for this purpose is for example catalytic hydrogenation, using, for example, Raney nickel, Pt/C, Pd/C or Rh/C, or reduction with iron powder, zinc powder, etc. in a mixture of organic acid, for example acetic acid or propionic acid, and a protic solvent, such as methanol, ethanol or water.

The nitrobenzenes can be synthesized by nitration, substitution reactions, etc. Scheme 3 exemplifies a synthetic sequence.

Scheme 3

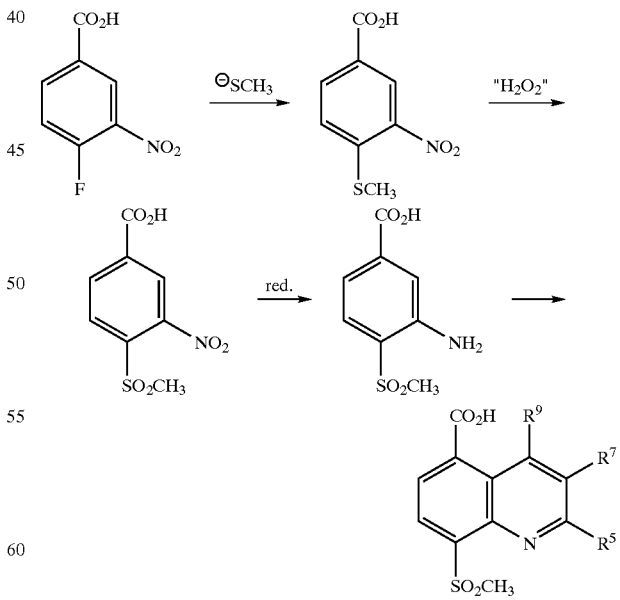

Isoquinolinecarboxylic acids can be synthesized for example from halogenated isoquinolines by halogen/cyanide exchange (Chem. Ber. 52 (1919), 1749) and subsequent hydrolysis. (Scheme 4)

Scheme 4

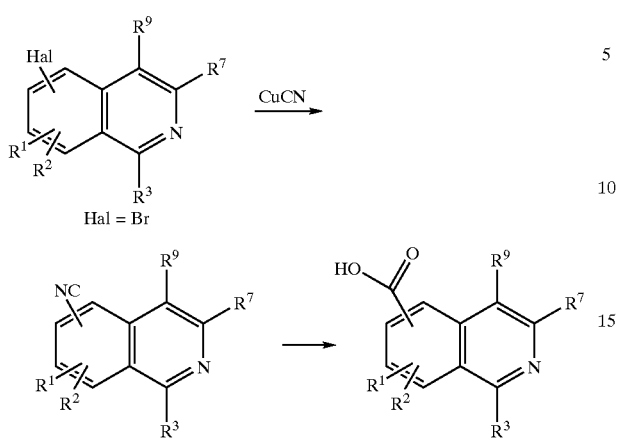

It is also possible to prepare the corresponding aminoisoquinolines from nitrated isoquinolines by reduction (as mentioned above). Subsequent diazotization, Sandmeyer reaction with cyanide and hydrolysis afford isoquinolinecarboxylic acids (Scheme 5).

Scheme 5

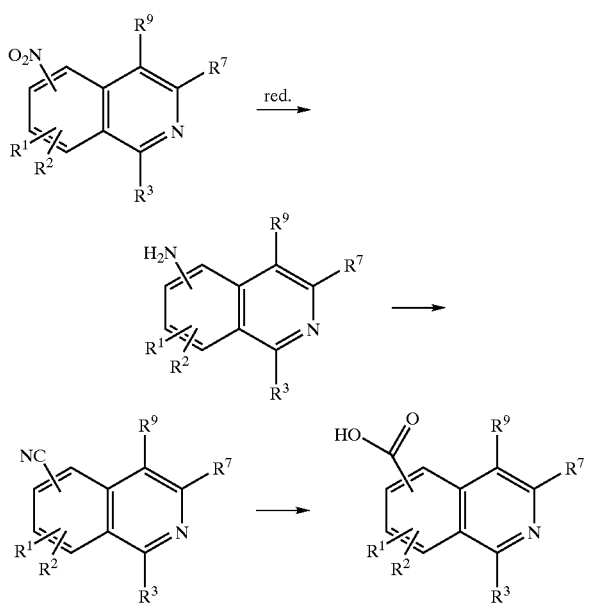

Halogenated or nitrated isoquinolines can be prepared according to EP-A 633 262. Furthermore, it is possible to obtain halogenated isoquinolines starting from unsubstituted or substituted benzaldehydes by reaction with aminoacetaldehyde acetal and subsequent halogenation (Helv. Chim. Acta 68 (1985), 1828) (Scheme 6).

Scheme 6

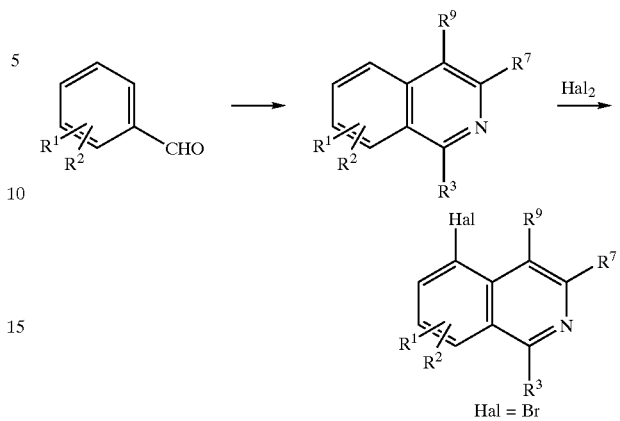

The N-oxides of the quinoline- or isoquinolinecarboxylic acids can be obtained from the corresponding quinoline- or isoquinolinecarboxylic acids by oxidation with hydrogen peroxide. It may be advantageous to convert the corresponding acids first into the $C_1$–$C_6$-alkyl esters, to carry out the oxidation with hydrogen peroxide and then hydrolyze the ester.

2,3-Dihydroquinoline derivatives can be obtained, inter alia, by cyclization of γ-functionalized N-alkylanilines, with or without using Lewis acids or protic acids (Heterocycles 24 (1986), 2109; J. Am. Chem. Soc. 71 (1949), 1901).

Tetrahydroisoquinoline derivatives can be obtained from isoquinolines by reduction with hydrogen, if appropriate by metal catalysis, for example by Pt in acetic acid. However, it is also possible to react isoquinolines with dimethyl sulfate and to convert them into tetrahydroisoquinoline derivatives by reduction with sodium borohydride.

PREPARATION EXAMPLES 2-(8-Bromoquinolin-5-yl)carbonyl-1,3-cyclohexanedione (Compound 5.02)

Step 1: 8-Bromo-5-quinolinecarbonyl Chloride 2.3 g of 8-bromo-5-quinolinecarboxylic acid were heated at reflux temperature together with 40 ml of toluene, 1 drop of dimethylformamide and 1.2 g of thionyl chloride for 1 hour. The solvent was then distilled off and the acyl chloride obtained was used directly for further reactions.

Step 2

0.9 g of 1,3-cyclohexanedione, 10 ml of methylene chloride and 0.9 g of triethylamine were charged initially, and 2.1 g of acyl chloride from Step 1 in 30 ml of methylene chloride were added dropwise at 0–10° C. Stirring was continued for 1 hour at room temperature. Thereafter, the reaction solution was diluted with water, acidified with hydrochloric acid and extracted with methylene chloride. The organic phase was dried and concentrated. The o-acylated intermediate was purified by chromatography over silica gel.

Yield: 1.2 g (Melting point: 118° C.)

Step 3

1.1 g of the O-acylated [sic] intermediate of Step 2 were dissolved in 30 ml of acetonitrile and then treated with 1.1 g of triethylamine and 0.2 g of acetone cyanohydrin. The mixture was stirred for 1 hour. The reaction solution was then poured into 2 N hydrochloric acid and extracted with ethyl acetate. The organic phase was then treated with sodium carbonate solution and the aqueous alkaline phase was acidified and extracted once more with ethyl acetate. The organic phase was dried, concentrated and purified by chromatography over silica gel.

Yield: 0.13 g
(Melting point: 180° C.)

2-(5-Nitroquinolin-8-yl)carbonylcyclohexane-1,3-dione (Compound 8.01)

1.0 g of 5-nitro-8-quinolinecarboxylic acid together with 0.5 g of 1,3-cyclohexanedione and 1.0 g of dicyclohexylcarbodiimide were stirred in 15 ml of acetonitrile at room temperature for about 12 hours. 0.7 g of triethylamine and 0.2 ml of acetone cyanohydrin were then added. After 4 hours, the reaction solution was poured into aqueous sodium carbonate solution and extracted with ethyl acetate. The aqueous phase was acidified with hydrochloric acid and extracted with ethyl acetate. The organic phase was dried, the solvent was distilled off and the residue was chromatographed over silica gel.

Yield: 0.14 g
($^1$H-NMR (CDCl$_3$, δ in ppm): 2.10 (2H); 2.36 (2H); 2.85 (2H); 7.62 (2H); 8.43 (1H); 8.93 (1H); 9.06 (1H); 16.39 (1H))

In addition to the hetaroyl derivatives of the formula I described above, further hetaroyl derivatives of the formula I which have been or can be prepared in a similar manner are listed in Tables 5–16 below:

TABLE 5

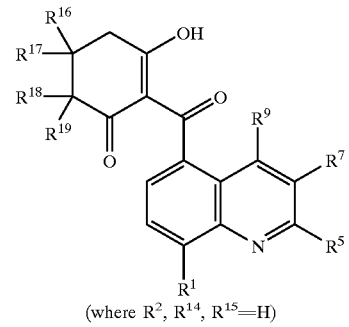

Ia (where $R^2$, $R^{14}$, $R^{15}$=H)

| No. | $R^1$ | $R^5$ | $R^7$ | $R^9$ | $R^{16}$ | $R^{17}$ | $R^{18}$ | $R^{19}$ | physical data mp[° C.]; $^1$H-NMR[ppm] |
|---|---|---|---|---|---|---|---|---|---|
| 5.01 | Br | H | H | H | CH$_3$ | CH$_3$ | H | H | 1.17(6H); 2.53(4H); 7.29(1H); 7.48(1H); 8.06(1H); 8.19(1H); 9.07(1H); |
| 5.02 | Br | H | H | H | H | H | H | H | 180 |
| 5.03 | CH$_3$ | H | H | H | H | H | H | H | 152 |
| 5.04 | OCH$_3$ | H | H | H | CH$_3$ | H | H | H | 134 |
| 5.05 | Cl | H | H | H | CH$_3$ | CH$_3$ | H | H | 112 |
| 5.06 | Cl | H | H | H | H | H | CH$_3$ | CH$_3$ | 110 |
| 5.07 | SO$_2$CH$_3$ | H | H | H | H | H | H | H | 190–195 |
| 5.08 | SO$_2$CH$_3$ | H | H | H | CH$_3$ | H | H | H | 117 |
| 5.09 | SO$_2$CH$_3$ | H | H | H | CH$_3$ | CH$_3$ | H | H | 84 |
| 5.10 | SO$_2$CH$_3$ | H | H | H | H | H | CH$_3$ | CH$_3$ | 95–98 |
| 5.11 | Cl | H | H | H | H | H | H | H | 175–179 |
| 5.12 | Cl | H | H | H | CH$_3$ | H | H | H | 1.16(3H); 2.18(1H); 2.37(1H); 2.56(2H); 2.91(1H); 7.38(1H); 7.49(1H); 7.86(1H); 8.20(1H); 9.06(1H); 16.70(1H); |
| 5.13 | CH$_3$ | H | H | H | H | H | CH$_3$ | CH$_3$ | 1.13(6H); 1.92(2H); 2.49(2H); 2.86(3H); 7.38(2H); 7.59(1H); 8.21(1H); 8.94(1H); 17.18(1H); |
| 5.14 | CH$_3$ | H | H | H | CH$_3$ | CH$_3$ | H | H | 1.11(6H); 2.47(4H); 2.81(3H); 7.42(2H); 7.55(1H); 8.32(1H); 8.93(1H); |
| 5.15 | OCH$_3$ | H | H | H | CH$_3$ | CH$_3$ | H | H | 172 |
| 5.16 | OCH$_3$ | H | H | H | H | H | CH$_3$ | CH$_3$ | 67 |
| 5.17 | OCH$_3$ | H | H | H | H | H | H | H | 148 |
| 5.18 | Br | H | H | H | CH$_3$ | H | H | H | 106 |
| 5.19 | Br | H | H | H | H | H | CH$_3$ | CH$_3$ | 115 |
| 5.20 | Cl | CH$_3$ | H | H | H | H | H | H | 199–200 |
| 5.21 | Cl | CH$_3$ | H | H | CH$_3$ | H | H | H | 189–191 |
| 5.22 | Cl | CH$_3$ | H | H | CH$_3$ | CH$_3$ | H | H | 153 |
| 5.23 | Cl | CH$_3$ | H | H | H | H | CH$_3$ | CH$_3$ | 144–146 |
| 5.24 | Cl | H | CH$_3$ | H | H | H | CH$_3$ | CH$_3$ | 124–128 |
| 5.25 | Cl | H | H | CH$_3$ | CH$_3$ | CH$_3$ | H | H | 139–141 |

TABLE 5-continued

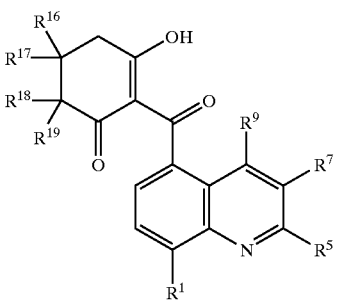

(where $R^2$, $R^{14}$, $R^{15}$=H)

| No. | $R^1$ | $R^5$ | $R^7$ | $R^9$ | $R^{16}$ | $R^{17}$ | $R^{18}$ | $R^{19}$ | physical data mp[° C.]; $^1$H-NMR[ppm] |
|---|---|---|---|---|---|---|---|---|---|
| 5.26 | Cl | H | CH$_3$ | H | H | H | H | H | 161–162 |
| 5.27 | F | H | H | H | H | H | H | H | 129–132 |
| 5.28 | F | H | H | H | CH$_3$ | CH$_3$ | H | H | 100 |
| 5.29 | Cl | H | CH$_3$ | H | CH$_3$ | H | H | H | 62–63 |
| 5.30 | Cl | CH$_3$ | CH$_3$ | H | H | H | H | H | 173 |
| 5.31 | Cl | CH$_3$ | CH$_3$ | H | CH$_3$ | CH$_3$ | H | H | 181 |
| 5.32 | Cl | H | Cl | H | H | H | H | H | |
| 5.33 | Cl | H | Cl | H | CH$_3$ | CH$_3$ | H | H | |

TABLE 6

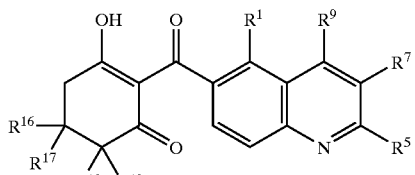

(where $R^2$, $R^{14}$, $R^{15}$=H and Z=$Z^1$)

| No. | $R^1$ | $R^5$ | $R^7$ | $R^9$ | $R^{16}$ | $R^{17}$ | $R^{18}$ | $R^{19}$ | physical data mp[° C.]; $^1$H-NMR[ppm] |
|---|---|---|---|---|---|---|---|---|---|
| 6.01 | NO$_2$ | H | H | H | H | H | CH$_3$ | CH$_3$ | |
| 6.02 | NO$_2$ | H | H | H | CH$_3$ | CH$_3$ | CH$_3$ | CH$_3$ | 1.25(s, 6H); 2.55(s, 2H); 3.05(s, 2H); 7.55(q, 1H); 8.05(d, 1H); 8.45(d, 1H); 8.75(d, 1H); 9.10(d, 1H) |
| 6.03 | NO$_2$ | H | H | H | H | H | H | H | |
| 6.04 | Cl | H | H | H | H | H | CH$_3$ | CH$_3$ | |
| 6.05 | Cl | H | H | H | CH$_3$ | CH$_3$ | H | H | 204 |
| 6.06 | Cl | H | H | H | H | H | H | H | 2.08(2H); 2.45(2H); 2.81(2H); 7.58(2H); 8.10(1H); 8.65(1H); 9.00(1H); 17.05(1H) |

TABLE 7

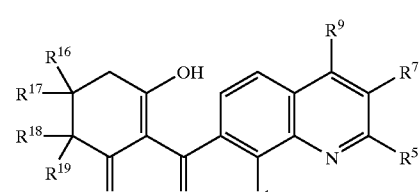

(where $R^2$, $R^{14}$, $R^{15}$=H)

| No. | $R^1$ | $R^5$ | $R^7$ | $R^9$ | $R^{16}$ | $R^{17}$ | $R^{18}$ | $R^{19}$ | physical data mp[° C.] |
|---|---|---|---|---|---|---|---|---|---|
| 7.01 | CH$_3$ | H | H | H | H | H | H | H | 110 |
| 7.02 | CH$_3$ | H | H | H | CH$_3$ | CH$_3$ | H | H | 130–133 |

TABLE 7-continued

Ib (where $R^2$, $R^{14}$, $R^{15}$=H)

| No. | $R^1$ | $R^5$ | $R^7$ | $R^9$ | $R^{16}$ | $R^{17}$ | $R^{18}$ | $R^{19}$ | physical data mp[° C.] |
|---|---|---|---|---|---|---|---|---|---|
| 7.03 | CH₃ | H | H | H | CH₃ | H | H | H | 106 |
| 7.04 | CH₃ | H | H | H | H | H | CH₃ | CH₃ | 110 |

TABLE 8

Ic (where $R^2$, $R^{14}$, $R^{15}$=H)

| No. | $R^1$ | $R^5$ | $R^7$ | $R^9$ | $R^{16}$ | $R^{17}$ | $R^{18}$ | $R^{19}$ | physical data mp[° C.]; ¹H-NMR[ppm] |
|---|---|---|---|---|---|---|---|---|---|
| 8.01 | NO₂ | H | H | H | H | H | H | H | 2.10(2H); 2.36(2H); 2.85(2H); 7.62(2H); 8.43(1H); 8.93(1H); 9.06(1H); 16.39(1H); |
| 8.02 | NO₂ | H | H | H | CH₃ | CH₃ | H | H | 188 |
| 8.03 | SO₂CH₃ | H | H | H | CH₃ | CH₃ | H | H | 137–138 |

TABLE 9

Id (where $R^2$, $R^{14}$, $R^{15}$=H)

| No. | $R^1$ | $R^3$ | $R^7$ | $R^9$ | $R^{16}$ | $R^{17}$ | $R^{18}$ | $R^{19}$ | physical data mp[° C.]; ¹H-NMR[ppm] |
|---|---|---|---|---|---|---|---|---|---|
| 9.01 | NO₂ | H | H | H | H | H | CH₃ | CH₃ | |
| 9.02 | Cl | H | H | H | H | H | CH₃ | CH₃ | |
| 9.03 | NO₂ | H | H | H | H | H | H | H | |
| 9.04 | Cl | H | H | H | H | H | H | H | |

TABLE 10

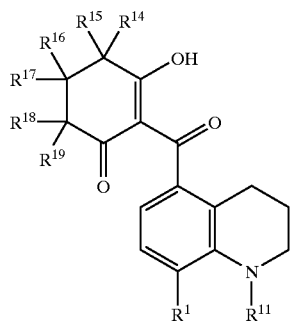

(where $R^2$, $R^5$, $R^6$, $R^7$, $R^8$, $R^9$, $R^{10}$=H)

| No. | $R^1$ | $R^{11}$ | $R^{14}$ | $R^{15}$ | $R^{16}$ | $R^{17}$ | $R^{18}$ | $R^{19}$ | physical data $^1$H-NMR[ppm] |
|---|---|---|---|---|---|---|---|---|---|
| 10.01 | CH$_3$ | CH$_3$ | H | H | H | H | CH$_3$ | CH$_3$ | |
| 10.02 | F | CH$_3$ | H | H | H | H | CH$_3$ | CH$_3$ | |
| 10.03 | Cl | CH$_3$ | H | H | H | H | CH$_3$ | CH$_3$ | |
| 10.04 | CH$_3$ | CH$_3$ | H | H | H | H | H | H | 1.0–2.6(10H); 2.28(3H); 2.65(3H); 3.09(2H); 6.59(1H); 6.95(1H); 17.5(1H) |
| 10.05 | F | CH$_3$ | H | H | H | H | H | H | |
| 10.06 | Cl | CH$_3$ | H | H | H | H | H | H | |
| 10.07 | CH$_3$ | COCH$_3$ | H | H | H | H | CH$_3$ | CH$_3$ | |
| 10.08 | F | COCH$_3$ | H | H | H | H | CH$_3$ | CH$_3$ | |
| 10.09 | Cl | COCH$_3$ | H | H | H | H | CH$_3$ | CH$_3$ | 1.1–2.0(14H); 2.00(3H); 2.30(3H); 2.65(2H); 2.90(2H); 4.80(2H); 7.00(1H); 7.15(1H); 17.9(1H) |
| 10.10 | F | COCH$_3$ | H | H | H | H | H | H | |
| 10.11 | Cl | COCH$_3$ | H | H | H | H | H | H | |
| 10.12 | CH$_3$ | COCH$_3$ | CH$_3$ | CH$_3$ | H | H | CH$_3$ | H | |

TABLE 11

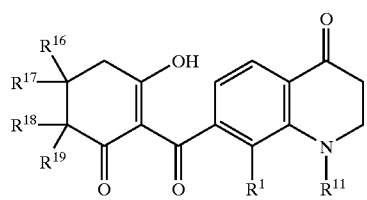

(where $R^2$, $R^5$, $R^6$, $R^7$, $R^8$, $R^{14}$, $R^{15}$=H; "CR$^9$R$^{10}$" = "C=O")

| No. | $R^1$ | $R^{11}$ | $R^{16}$ | $R^{17}$ | $R^{18}$ | $R^{19}$ | physical data mp[° C.]; $^1$H-NMR[ppm] |
|---|---|---|---|---|---|---|---|
| 11.01 | CH$_3$ | COCH$_3$ | H | H | H | H | 68 |
| 11.02 | CH$_3$ | COCH$_3$ | CH$_3$ | H | H | H | 73 |
| 11.03 | CH$_3$ | COCH$_3$ | CH$_3$ | CH$_3$ | H | H | 54 |
| 11.04 | H | COCH$_3$ | H | H | H | H | 1.79(2H); 2.28(3H); 2.48(4H); 2.80(2H); 4.16(2H); 7.58(1H); 7.89(1H); 8.02(1H) |

TABLE 12

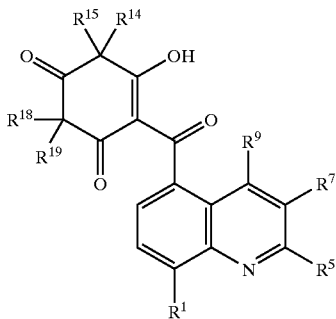

(where $R^2$=H, "$CR^{16}R^{17}$" = "C=O")

| No. | $R^1$ | $R^5$ | $R^7$ | $R^9$ | $R^{14}$ | $R^{15}$ | $R^{18}$ | $R^{19}$ | physical data mp[° C.]; $^1$H-NMR[ppm] |
|---|---|---|---|---|---|---|---|---|---|
| 12.01 | $CH_3$ | H | H | H | $CH_3$ | $CH_3$ | $CH_3$ | $CH_3$ | 91–95 |
| 12.02 | Cl | H | $CH_3$ | H | $CH_3$ | $CH_3$ | $CH_3$ | $CH_3$ | 1.35(6H); 1.60(6H); 2.55(3H); 7.31(1H); 7.72(1H); 7.95(1H); 8.91(1H); 17.7(1H) |
| 12.03 | F | H | H | H | $CH_3$ | $CH_3$ | $CH_3$ | $CH_3$ | 121 |
| 12.04 | $SO_2CH_3$ | H | H | H | $CH_3$ | $CH_3$ | $CH_3$ | $CH_3$ | 200 |
| 12.05 | Cl | H | H | H | $CH_3$ | $CH_3$ | $CH_3$ | $CH_3$ | 60 |
| 12.06 | Br | H | H | H | $CH_3$ | $CH_3$ | $CH_3$ | $CH_3$ | 1.35(gH); 1.65(6H); 7.22(1H); 7.47(1H); 8.07(1H); 8.24(1H); 9.10(1H); 17.8(1H) |
| 12.07 | Cl | $CH_3$ | H | H | $CH_3$ | $CH_3$ | $CH_3$ | $CH_3$ | 65 |
| 12.08 | $OCH_3$ | H | H | H | $CH_3$ | $CH_3$ | $CH_3$ | $CH_3$ | 88 |
| 12.09 | $SO_2CH_3$ | $CH_3$ | H | H | $CH_3$ | $CH_3$ | $CH_3$ | $CH_3$ | 1.28(6H); 2.60(3H); 3.66(3H); 6.50(1H); 7.00(1H); 8.05(1H); 8.20(1H) |
| 12.10 | Cl | H | Cl | H | $CH_3$ | $CH_3$ | $CH_3$ | $CH_3$ | |
| 12.11 | Cl | H | Br | H | $CH_3$ | $CH_3$ | $CH_3$ | $CH_3$ | |
| 12.12 | Br | H | $CH_3$ | H | $CH_3$ | $CH_3$ | $CH_3$ | $CH_3$ | |
| 12.13 | $SO_2CH_3$ | H | $CH_3$ | H | $CH_3$ | $CH_3$ | $CH_3$ | $CH_3$ | 1.25(6H); 2.21(3H); 3.58(3H); 7.15(1H); 8.05(1H); 8.22(1H); 8.81(1H) |
| 12.14 | Br | $CH_3$ | H | H | $CH_3$ | $CH_3$ | $CH_3$ | $CH_3$ | 1.32(6H); 1.55(6H); 2.80(3H); 7.16(1H); 7.33(1H); 8.00(1H); 8.10(1H) |

TABLE 13

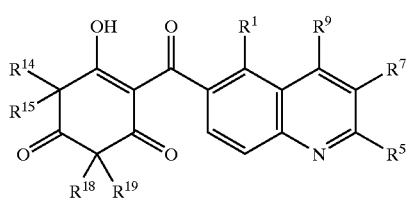

(where $R^2$=H, "$CR^{16}R^{17}$" = "C=O" and Z=$Z^1$)

| No. | $R^1$ | $R^5$ | $R^7$ | $R^9$ | $R^{14}$ | $R^{15}$ | $R^{18}$ | $R^{19}$ | physical data mp[° C.] |
|---|---|---|---|---|---|---|---|---|---|
| 13.01 | $NO_2$ | H | H | H | $CH_3$ | $CH_3$ | $CH_3$ | $CH_3$ | |
| 13.02 | Cl | H | H | H | $CH_3$ | $CH_3$ | $CH_3$ | $CH_3$ | |

TABLE 14

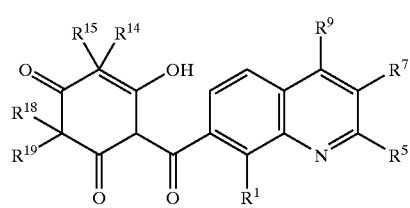

(where $R^2$=H, "$CR^{16}R^{17}$"= "C=O")

| No. | $R^1$ | $R^5$ | $R^7$ | $R^9$ | $R^{14}$ | $R^{15}$ | $R^{18}$ | $R^{19}$ | physical data mp[° C.] |
|---|---|---|---|---|---|---|---|---|---|
| 14.01 | $CH_3$ | H | H | H | $CH_3$ | $CH_3$ | $CH_3$ | $CH_3$ | 82 |

TABLE 15

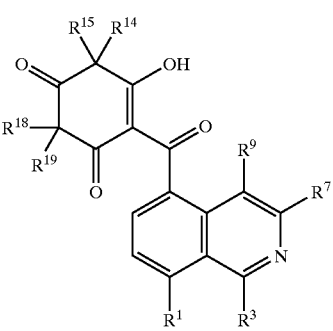

Id (where $R^2 = H$, "$CR^{16}R^{17}$" = "$C=O$")

| No. | $R^1$ | $R^3$ | $R^7$ | $R^9$ | $R^{14}$ | $R^{15}$ | $R^{18}$ | $R^{19}$ | physical data mp [° C.] |
|---|---|---|---|---|---|---|---|---|---|
| 15.01 | $NO_2$ | H | H | H | $CH_3$ | $CH_3$ | $CH_3$ | $CH_3$ | |
| 15.02 | Cl | H | H | H | $CH_3$ | $CH_3$ | $CH_3$ | $CH_3$ | |

TABLE 16

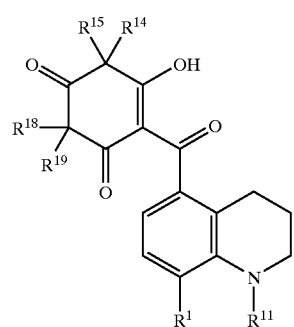

If (where $R^2, R^5, R^6, R^7, R^8, R^9, R^{10}$ = H; "$CR^{16}R^{17}$" = "$C=O$")

| No. | $R^1$ | $R^{11}$ | $R^{14}$ | $R^{15}$ | $R^{18}$ | $R^{19}$ | physical data mp (° C.) |
|---|---|---|---|---|---|---|---|
| 16.01 | $CH_3$ | $CH_3$ | $CH_3$ | $CH_3$ | $CH_3$ | $CH_3$ | 120 |
| 16.02 | Cl | $CH_3$ | $CH_3$ | $CH_3$ | $CH_3$ | $CH_3$ | |
| 16.03 | F | $CH_3$ | $CH_3$ | $CH_3$ | $CH_3$ | $CH_3$ | |
| 16.04 | $CH_3$ | $COCH_3$ | $CH_3$ | $CH_3$ | $CH_3$ | $CH_3$ | |
| 16.05 | Cl | $COCH_3$ | $CH_3$ | $CH_3$ | $CH_3$ | $CH_3$ | |
| 16.06 | F | $COCH_3$ | $CH_3$ | $CH_3$ | $CH_3$ | $CH_3$ | |

The syntheses of some carboxylic acids of the formula IIIb are listed below:

8-Methylsulfonyl-5-quinolinecarboxylic Acid (Compound 17.06)

Step 1: 3-Nitro-4-(methylthio)benzoic Acid 0.75 mol of 4-fluoro-3-nitrobenzoic acid was charged in 2 l of methanol, and 0.75 mol of sodium methoxide was added dropwise. 0.83 mol of sodium thiomethoxide was then added and the reaction mixture was heated at from 55 to 60° C. for 5 hours. After cooling, 1 l of water was added, the precipitate was filtered off with suction and washed with 100 ml of methylene chloride. The residue was then taken up in 500 ml of 2 N hydrochloric acid and the precipitate formed was filtered off with suction and washed with water. The residue was then taken up in tetrahydrofuran and dried over sodium sulfate and the solvent was distilled off.

Yield: 127.6 g (79%) (yellow solid)
(Melting point: 245–247° C.)

Step 2: 3-Nitro-4-methylsulfonylbenzoic Acid 0.22 mol of 3-nitro-4-(methylthio)benzoic acid was charged together with 800 ml of glacial acetic acid and 5.4 g of $Na_2WO_4.2 H_2O$. At a temperature of 55° C., 1.32 mol of $H_2O_2$ (30% strength) were added dropwise. The mixture was then stirred for 20 minutes at 50° C. and for 2 hours at 70° C. After cooling, the reaction solution was stirred into 1 l of water, the precipitate was filtered off with suction, the residue was washed with water and the product was dried under reduced pressure.

Yield: 47.4 g (88%) (white crystals)
(IR ($\nu$ in $cm^{-1}$): 1699, 1558, 1371, 1322, 1155)

Step 3: 3-Amino-4-methylsulfonylbenzoic Acid 0.447 mol of 3-nitro-4-methylsulfonylbenzoic acid was reduced with hydrogen by employing 100 g of Raney nickel in 2.5 l of methanol. The mixture was then heated to reflux and filtered off hot with suction. The filtrate was concentrated.

Yield: 88.1 g (91%)
($^1$H-NMR ($d_6$-DMSO, δ in ppm): 3.18 (3H); 6.25 (2H); 7.21 (1H); 7.48 (1H); 7.72 (1H); 13.8 (1H))

Step 4: 8-Methylsulfonyl-5-quinolinecarboxylic Acid 38 ml of water and 102 g of concentrated sulfuric acid were heated to 110° C. At 95° C., 0.25 mol of 3-amino-4-methylsulfonylbenzbic acid was added. The mixture was then heated to 140° C., and 0.8 g of sodium iodide and 0.3 mol of glycerol were added. The reaction temperature was then increased to 150° C. While the mixture was heated to and stirred at 150° C. (1 hour), 47 g of distillate were collected. After cooling, the reaction mixture was carefully admixed with 200 ml of water and diluted with a further 800 ml of water. Using 20% strength aqueous sodium hydroxide solution, the pH was adjusted to 13 and the mixture was filtered and adjusted to pH 3.5 with sulfuric acid. This procedure was repeated. A precipitate was formed which was filtered off with suction. The filtrate was adjusted to pH=2 and the resulting precipitate was filtered off with suction, washed with water and dried.

Yield: 44.9 g (71%)
($^1$H-NMR ($d_6$-DMSO, δ in ppm): 3.70 (3H); 7.82 (1H); 8.40 (1H); 8.68 (1H); 9.32 (1H); 9.66 (1H), 14.01 (1H))

8-Bromoquinoline-5-carboxylic Acid (Compound 17.05)

Step 1: 5-Amino-8-bromoquinoline

At reflux, 10.0 g of 8-bromo-5-nitroquinoline in 68 ml of glacial acetic acid and 34 ml of ethanol were added dropwise to a mixture of 7.75 g of iron powder, 18 ml of glacial acetic acid and 9 ml of ethanol. After stirring for 45 minutes at reflux, the mixture was cooled and filtered through diatomaceous earth. The filtrate was concentrated, taken up in methylene chloride, washed with sodium carbonate solution, dried and concentrated.

Yield: 7.90 g
($^1$H-NMR ($CDCl_3$; δ in ppm): 4.22 (bs, 2H); 7.71 (m,1H); 7.40 (m,1H); 7.80 (m,1H); 8.18 (m,1H); 9.00 (m,1H))

Step 2: 8-Bromo-5-cyanoquinoline 0.60 g of concentrated hydrochloric acid was added dropwise to a mixture of 0.70 g of 5-amino-8- bromoquinoline and 3.15 ml of acetic acid, and the mixture was stirred for 1 hour at room temperature. At 0–5° C., 0.22 g of sodium nitrite in 0.45 ml of water were then added, and the mixture was stirred for 1 hour. After the addition of 20 mg of urea in 0.16 ml of water, stirring was continued at 0–5° C. for a further hour. This solution is added to a two-phase system of toluene/copper(I) cyanide solution which was prepared as follows: a solution of 0.79 g of copper(II) sulfate in 2.2 ml of water was added dropwise to a solution of 1.06 g of 10% strength ammonia solution and 0.77 g of sodium cyanide, and 6 ml of toluene were added to this mixture to form a lower layer. After stirring for 1 hour at room temperature, insoluble particles were filtered off and the solution was extracted with ethyl acetate. The organic phase was dried and the solvent was removed under reduced pressure.

Yield: 0.50 g ($^1$H-NMR (CDCl$_3$; δ in ppm): 7.61 (m,1H); 7.76 (m,1H); 8.19 (m,1H); 8.59 (m,1H); 9.17 (m,1H))

Step 3: 8-Bromoquinoline-5-carboxylic Acid

At 150° C., 5.0 g of 8-bromo-5-cyanoquinoline were added a little at a time to 10.10 g of 75% strength sulfuric acid. After one hour, the reaction mixture was cooled, poured into ice water and extracted with ethyl acetate. The organic phase was dried and concentrated.

Yield: 3.6 g ($^1$H-NMR (d$_6$-DMSO; δ in ppm): 7.80 (m,1H); 8.18 (m,1H); 8.30 (m,1H); 9.15 (m,1H); 9.40 (m,1H))

5-Nitroquinoline-6-carboxylic Acid
(Compound 18.01)

Step 1: 5-Nitro-6-methylquinoline 2.45 mol of 6-methylquinoline were added to 1 l of concentrated sulfuric acid, and 2.94 mol of 65% strength nitric acid were added dropwise at from 0 to 10° C. The mixture was stirred for one hour, poured onto ice, adjusted to pH 2.5 using aqueous sodium hydroxide solution, filtered off with suction, washed with water and dried over magnesium sulfate.

Yield: 313.0 g of colorless crystals ($^1$H-NMR (CDCl$_3$; δ in ppm): 2.55 (s,3H); 7.55 (q,1H); 7.60 (d,1H); 8.10 (d,1H); 8.15 (d,1H); 8.95 (q,1H)

Step 2: 5-Nitroquinoline-6-carboxylic Acid 20.0 g of vanadium pentoxide and 0.74 mol of 5-nitro-6-methylquinoline were added to 1.3 l of sulfuric acid and 200 ml of 65% strength nitric acid were metered in at 140° C. over a period of 40 hours using a metering pump. The solution was subsequently poured onto ice, adjusted to pH 8.0 using aqueous sodium hydroxide solution, filtered off with suction and dried over magnesium sulfate. 81.0 g of starting material was recovered. The mother liquor was adjusted to pH 2.5 with sulfuric acid, filtered off with suction and dried over magnesium sulfate.

Yield: 67.0 g of colorless crystals ($^1$H-NMR (d$_6$-DMSO; δ in ppm): 7.80 (q,1H); 8.20 (d,1H); 8.25 (d,1H); 8.40 (d,1H); 9.20 (d,1H)

5-Nitroquinoline-8-carboxylic Acid
(Compound 20.03)

Step 1: 8-Cyano-5-nitroquinoline 5.80 g of 8-bromo-5-nitroquinoline and 2.00 g of copper (I) cyanide in 15 ml of dimethylformamide were heated to 150° C. for 5 hours. After cooling, methylene chloride was added, insoluble particles were filtered off and the filtrate was concentrated.

Yield: 3.90 g ($^1$H-NMR (CDCl$_3$; δ in ppm): 7.84 (m,1H); 8.37 (m,1H); 8.40 (m,1H); 9.00 (m,1H); 9.24 (m,1H))

Step 2: 5-Nitroquinoline-8-carboxylic Acid

At 150° C., 1.50 g of 8-cyano-5-nitroquinoline were added a little at a time to 3.50 g of 75% strength sulfuric acid. After stirring for one hour, the reaction mixture was cooled, poured into ice water and extracted with ethyl acetate. The organic phase was dried and the solvent was removed under reduced pressure.

Yield: 1.1 g (Melting point: 210° C.)

($^1$H-NMR (d$_6$-DMSO; δ in ppm): 8.00 (m,1H); 8.49 (m,1H); 8.58 (m,1H); 9.01 (m,1H); 9.22 (m,1H); 15.0 (bs, 1H))

8-Dimethyl-1,2,3,4-tetrahydroquinoline-5-carboxylic Acid
(Compound 22.01)

Step 1: 8-Methyl-1,2,3,4-tetrahydroquinoline-5-carboxylic Acid 0.1 mol of 8-methylquinoline-5-carboxylic acid was suspended in 1.5 l of ethanol and admixed with 10.0 g of palladium on activated carbon (5%). In an autoclave, the mixture was reduced at 50° C. with hydrogen (1 bar) over a period of 48 hours (HPLC monitoring). The reaction mixture was subsequently filtered, the filter cake was washed with ethanol and the combined organic filtrates were concentrated.

Yield: 17.4 g of a yellow solid ($^1$H-NMR (d$_6$-DMSO; δ in ppm): 1.75 (m,2H); 2.05 (s,3H); 2.90 (m,2H); 3.25 (m,2H); 5.10 (brs,2H); 6.80 (d,1H); 6.90 (d,1H)

(Melting point: 130° C.)

Step 2: 1,8-Dimethyl-1,2,3,4-tetrahydroquinoline-5-carboxylic Acid 24 mmol of sodium cyanoborohydride w&e added to 5 mmol of 8-methyl-1,2,3,4-tetrahydroquinoline-5-carboxylic acid and 50 mmol of paraformaldehyde in 30 ml of glacial acetic acid, the temperature of the reaction mixture being kept below 30° C. using an ice bath. The reaction mixture was stirred at room temperature for 15 hours, poured onto ice and adjusted to pH 4 with aqueous sodium hydroxide solution. The mixture was then extracted with ethyl acetate and the organic phase was washed with water, dried over sodium sulfate and concentrated.

Yield: 0.75 g of colorless crystals ($^1$H-NMR (d$_6$-DMSO; δ in ppm): 1.75 (m,2H); 2.25 (d,3H); 2.65 (s,3H); 3.00 (m,4H); 7.05 (d,1H); 7.30 (d,1H))

1-Acetyl-2,3-dihydro-4-quinolone-7-carboxylic Acid
(Compound 23.02)

Step 1: N-(2-Cyanoethyl)-3-aminobenzoic Acid 200.0 g of 3-aminobenzoic acid in 2 l of water were admixed with 53.2 g of sodium hydroxide. At 30° C., 126.6 g of acrylonitrile were added dropwise, and the mixture was then heated under reflux for 22 hours. The mixture was then cooled to 5° C. and acetic acid was added (pH=5) and the precipitate which had formed was filtered off with suction and washed with water.

Yield: 266.3 g ($^1$H-NMR (d$_6$-DMSO; δ in ppm): 2.75 (2H); 3.38 (2H); 6.21 (1H); 6.87 (1H); 7.21 (2H); 12.70 (1H))

Step 2: N-(2-Carboxyethyl)-3-aminobenzoic Acid 266.0 g of N-(2-cyanoethyl)-3-aminobenzoic acid together with 336.0 g of sodium hydroxide in 3 l of water were heated under ref lux for 5 hours. After cooling, the pH was adjusted to 3 with hydrochloric acid, the mixture was cooled and the precipitate was filtered off with suction.

Yield: 269.2 g (Melting point: 211° C.)

Step 3: 2,3-Dihydro-4-quinolone-7-carboxylic Acid

At 110° C., 50.0 g of the carboxylic acid of Step 2 were added a little at a time to 500.0 g of polyphosphoric acid. Stirring was continued for 1 hour. The reaction mixture was then poured onto ice, the precipitate was separated off and the mixture was extracted with ethyl acetate. The organic phase was then dried and concentrated.

Yield: 9.2 g ($^1$H-NMR (d$_6$-DMSO; δ in ppm): 2.52 (2H); 3.41 (2H); 7.05 (2H); 7.40 (1H); 7.65 (1H))

Step 4: 1-Acetyl-2,3-dihydro-4-quinolone-7-carboxylic Acid 5.0 g of 2,3-dihydro-4-quinolone-7-carboxylic acid and 22.5 g of acetic anhydride were heated to 100° C. for 1 hour. After cooling, water was added and the mixture was extracted with methylene chloride. The organic phase was dried and concentrated.

Yield: 4.8 g (Melting point: 150° C.)

In addition to the carboxylic acids of the formula IIIb described above, further carboxylic acids of the formula IIIb which were or can be prepared in a similar manner are listed in Tables 17–24 below:

TABLE 17

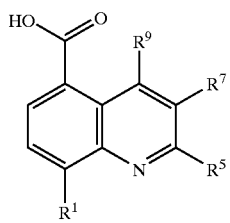

IIIb

| No. | R$^1$ | R$^5$ | R$^7$ | R$^9$ | physical data $^1$H-NMR [ppm]; mp [° C.] |
|---|---|---|---|---|---|
| 17.01 | F | H | H | H | 7.66(m, 1H); 7.80(m, 1H); 8.30(m, 1H); 9.01(m, 1H); 9.55(m, 1H); |
| 17.02 | Cl | H | H | H | 7.80(m, 1H); 8.09(m, 1H); 8.25(m, 1H); 9.10(m, 1H); 9.41(m, 1H); 13.1(bs, 1H); |
| 17.03 | Cl | H | CH$_3$ | H | 2.56(s, 3H); 7.91(m, 1H); 8.15(m, 1H); 8.96(m, 1H); 9.16(m, 1H); 13.1(bs, 1H); |

TABLE 17-continued

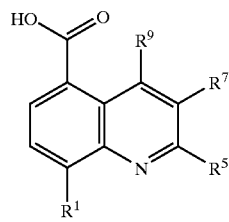

IIIb

| No. | R$^1$ | R$^5$ | R$^7$ | R$^9$ | physical data $^1$H-NMR [ppm]; mp [° C.] |
|---|---|---|---|---|---|
| 17.04 | Cl | CH$_3$ | H | H | 2.73(s, 3H); 7.49(m, 1H); 7.65(m, 1H); 8.14(m, 1H); 9.23(m, 1H); 13.1(bs, 1H); |
| 17.05 | Br | H | H | H | 7.80(m, 1H); 8.18(m, 1H); 8.30(m, 1H); 9.15(m, 1H); 9.40(m, 1H); |
| 17.06 | SO$_2$CH$_3$ | H | H | H | 3.70(s, 3H); 7.82(m, 1H); 8.40(m, 1H); 8.68(m, 1H); 9.32(m, 1H); 9.66(m, 1H); 14.01(bs, 1H); |
| 17.07 | SO$_2$CH$_3$ | H | CH$_3$ | H | 2.60(s, 3H); 3.63(s, 3H); 8.26(m, 1H); 8.40(m, 1H); 9.10(m, 1H); 9.14(m, 1H); |
| 17.08 | SO$_2$CH$_3$ | CH$_3$ | H | H | 2.80(m, 3H); 3.66(s, 3H); 7.70(m, 1H); 8.28(m, 1H); 8.45(m, 1H); 9.16(m, 1H); |
| 17.09 | CH$_3$ | H | H | H | 290 |
| 17.10 | OH | H | H | H | 7.39(m, 1H); 7.90(m, 1H); 8.33(m, 1H); 8.89(m, 1H); 9.70(m, 1H); |
| 17.11 | OCH$_3$ | H | H | H | 4.04(s, 3H); 7.33(m, 1H); 7.68(m, 1H); 8.31(m, 1H); 8.90(m, 1H); 9.60(m, 1H); |

TABLE 18

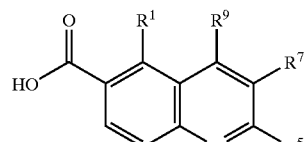

IIIb

| No. | R$^1$ | R$^5$ | R$^7$ | R$^9$ | physical data $^1$H-NMR [ppm] |
|---|---|---|---|---|---|
| 18.01 | NO$_2$ | H | H | H | 7.80(q, 1H); 8.20(d, 1H); 8.25(d, 1H); 8.40(d, 1H); 9.20(d1H) |
| 18.02 | Cl | H | H | H | |
| 18.03 | Br | H | H | H | |

TABLE 19

IIIb

| No. | $R^1$ | $R^5$ | $R^7$ | $R^9$ | physical data $^1$H-NMR [ppm] |
|---|---|---|---|---|---|
| 19.01 | $CH_3$ | H | H | H | 3.01(s, 3H); 7.64(m, 1H); 7.93(m, 1H); 8.42(m, 2H); 9.01(m, 1H); 13.30(bs, 1H); |

TABLE 20

IIIb

| No. | $R^1$ | $R^5$ | $R^7$ | $R^9$ | physical data mp [° C] |
|---|---|---|---|---|---|
| 20.01 | Cl | H | H | H | 199 |
| 20.02 | $SO_2CH_3$ | H | H | H | 231 |
| 20.03 | $NO_2$ | H | H | H | 210 |
| 20.04 | H | H | H | H | 177 |

TABLE 21

IIIb

| No. | $R^1$ | $R^3$ | $R^7$ | $R^9$ | physical data mp [° C.]; $^1$H-NMR [ppm] |
|---|---|---|---|---|---|
| 21.01 | $NO_2$ | H | H | H | |
| 21.02 | Cl | H | H | H | |

TABLE 22

| No. | $R^1$ | $R^{11}$ | physical data mp [° C.]; $^1$H-NMR [ppm] |
|---|---|---|---|
| 22.01 | $CH_3$ | $CH_3$ | 1.75(m, 2H); 2.25(s, 3H); 2.65(s, 3H); 3.00(m, 4H); 7.05(d, 1H); 7.30(d, 1H) |
| 22.02 | F | $CH_3$ | |
| 22.03 | $CH_3$ | $CH_3CO$ | 182 |
| 22.04 | F | $CH_3CO$ | |

TABLE 23

IIIb

| No. | $R^1$ | $R^{11}$ | physical data $^1$H-NMR [ppm]; mp [° C.] |
|---|---|---|---|
| 23.01 | H | H | 2.52(m, 2H); 3.42(m, 2H); 7.10(m, 1H); 7.37(m, 1H); 7.61(m, 1H); 12.8(s, 1H); |
| 23.02 | H | $COCH_3$ | 150 |
| 23.03 | $CH_3$ | $COCH_3$ | 2.20(s, 3H); 2.48(m, 2H); 2.70(s, 3H); 3.11(m, 2H); 3.86(m, 1H); 4.39(m, 1H); 7.61(m, 1H); 7.79(m, 1H); 12.80(bs, 1H); |

TABLE 24

IIIb

| No. | $R^1$ | $R^{11}$ | physical data $^1$H-NMR [ppm] |
|---|---|---|---|
| 24.01 | H | $COCH_3$ | 2.36(s, 3H); 2.85(m, 2H); 4.17(m, 2H); 7.89(m, 1H); 8.09(m, 1H); 8.40(m, 1H); 13.1(bs,1H); |

The compounds I and their agriculturally useful salts are suitable as herbicides, both in the form of isomer mixtures and in the form of the pure isomers. The herbicidal compositions comprising compounds I are capable of controlling vegetation on non-crop areas very efficiently, especially at high application rates. In crops such as wheat, rice, maize, soya and cotton, they act against broad-leaved weeds and grass weeds without causing any significant damage to the crop plants. This effect is observed mainly at low application rates.

Depending on the application method employed, the compounds I, or the herbicidal compositions comprising them, can additionally be employed in a further number of crop plants for eliminating undesirable plants. Examples of suitable crops are the following: *Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N.rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum,* Sorghum bicolor (*s. vulgare*), *Theobroma cacao, Trifolium pratense, Triticum aestivum, Triticum durum, Vicia faba, Vitis vinifera* and *Zea mays.*

In addition, the compounds I can also be used in crops which tolerate the action of herbicides owing to breeding including genetic engineering methods.

The compounds I, or the herbicidal compositions comprising them, can be used for example in the form of directly sprayable aqueous solutions, powders, suspensions, also highly concentrated aqueous, oily or other suspensions or dispersions, emulsions, oil dispersions, pastes, dusts, materials for spreading or granules by means of spraying, atomizing, dusting, spreading or watering. The use forms depend on the intended purposes; in any case, they should ensure the finest possible distribution of the active ingredients according to the invention.

Suitable inert auxiliaries are essentially: mineral oil fractions of medium to high boiling point, such as kerosine or diesel oil, further coal tar oils and oils of vegetable or animal origin, aliphatic, cyclic and aromatic hydrocarbons, eg. paraffins, tetrahydronaphthalene, alkylated naphthalenes or their derivatives and alkylated benzenes or their derivatives, alcohols, such as methanol, ethanol, propanol, butanol and cyclohexanol, ketones, such as cyclohexanone, or strongly polar solvents, eg. amines, such as N-methylpyrrolidone, or water.

Aqueous use forms can be prepared from emulsion concentrates, suspensions, pastes, wettable powders or water-dispersible granules by adding water. To prepare emulsions, pastes or oil dispersions, the substrates [sic], as such or dissolved in an oil or solvent, can be homogenized in water by means of a wetting agent, tackifier, dispersant or emulsifier. Alternatively, it is possible to prepare concentrates composed of active substance, wetting agent, tackifier, dispersant or emulsifier and, if desired, solvent or oil, these concentrates being suitable for dilution with water.

Suitable surfactants (adjuvants) are the alkali metal salts, alkaline earth metal salts and ammonium salts of aromatic sulfonic acids, eg. ligno-, phenol-, naphthalene- and dibutylnaphthalenesulfonic acid, and of fatty acids, of alkyl- and alkylarylsulfonates, of alkyl, lauryl ether and fatty alcohol sulfates, and the salts of sulfated hexa-, hepta- and octadecanols and of fatty alcohol glycol ether, condensates of sulfonated naphthalene and its derivatives with formaldehyde, condensates of naphthalene, or of naphthalenesulfonic acids, with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or grinding the active substances together with a solid carrier.

Granules, eg. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin, such as cereal meal, tree bark meal, wood meal and nutshell meal, cellulose powders, or other solid carriers.

The concentrations of the active ingredients I in the ready-to-use preparations can be varied within wide ranges. In general, the formulations comprise, for instance, from 0.001 to 98% by weight, preferably 0.01 to 95% by weight, of at least one active ingredient. The active ingredients are employed in a purity of from 90% to 100%, preferably 95% to 100% (according to NMR spectrum).

The following Formulation Examples illustrate the preparation of such formulations:

I. 20 parts by weight of the compound No. 5.02 are dissolved in a mixture composed of 80 parts by weight of alkylated benzene, 10 parts by weight of the adduct of 8 to 10 mol of ethylene oxide and 1 mol of oleic acid N-monoethanolamide, 5 parts by weight of calcium dodecylbenzenesulfonate and 5 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

II. 20 parts by weight of the compound No. 5.04 are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene 10 oxide and 1 mol of castor oil. Pouring the solution into 100,000 parts by weight of water and finely distributing it therein gives an aqueous dispersion which comprises 0.02% by weight of the live ingredient.

III. 20 parts by weight of the active ingredient No. 5.07 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. 5.11 are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel and the mixture is ground in a hammer mill. Finely distributing the mixture in 20,000 parts by weight of water gives a spray mixture which comprises 0.1% by weight of the active ingredient.

V. 3 parts by weight of the active ingredient No. 7.02 are mixed with 97 parts by weight of finely divided kaolin. This gives a dust which comprises 3% by weight of the active ingredient.

VI. 20 parts by weight of the active ingredient No. 8.02 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the active ingredient No. 5.20 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the active ingredient No. 5.26 is dissolved in a mixture composed of 80 parts by weight of cyclohexanone and 20 parts by weight of Wettol® EM 31 (=nonionic emulsifier based on ethoxylated castor oil; BASF AG). This gives a stable emulsion concentrate.

The herbicidal compositions or the active ingredients can be applied pre- or post-emergence. If the active ingredients are less well tolerated by certain crop plants, application techniques may be used in which the herbicidal compositions are sprayed, with the aid of spraying apparatus, in such a way that they come into as little contact as possible, if any, with the leaves of the sensitive crop plants, while the active ingredients reach the leaves of undesirable plants which grow underneath, or the exposed soil surface (post-directed, lay-by). Depending on the intended purpose, the season, the target plants and the growth stage, the application rates of active ingredient of the formula I are from 0.001 to 3.0, preferably 0.01 to 1.0, kg of active substance (a.s.) per ha.

To widen the spectrum of action and to achieve synergistic effects, the hetaroyl derivatives of the formula I can be mixed with a large number of representatives of other groups of herbicidal or growth-regulating active ingredients and applied jointly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids, and their derivatives, benzoic acid and its derivatives, benzothiadiazinones, 2-(het)aroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- or hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonyl-ureas, triazines, triazinones, triazolinones, triazolecarboxamides and uracils.

Furthermore, it may be advantageous to employ the compounds of the formula I, on their own or in combination with other herbicides, also in a mixture with other crop protection agents, for example pesticides or agents for controlling phytopathogenic fungi or bacteria. Also of interest is the miscibility with mineral salt solutions which are employed for treating nutritional and trace element deficiencies. Nonphytotoxic oils and oil concentrates may also be added.

Use Examples

The herbicidal activity of the hetaroyl derivatives of the formula I was demonstrated by the following greenhouse experiments:

The culture containers used were plastic flowerpots containing loamy sand with approximately 3.0% of humus as the substrate. The seeds of the test plants were sown separately for each species.

In the case of pre-emergence treatment, the active ingredients, which were suspended or emulsified in water, were applied directly after sowing by means of finely distributing nozzles. The containers were irrigated gently to promote germination and growth and subsequently covered with transluscent plastic hoods until the plants had rooted. This cover causes uniform germination of the test plants unless this was [sic] adversely affected by the active ingredients.

For the post-emergence treatment, the test plants were first grown to a plant height of from 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment. The application rate for the post-emergence treatment was 0.5 or 0.25 kg of a.s. (active substance) per ha.

Depending on the species, the plants were kept at from 10 to 25° C. or 20 to 35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage or normal course of growth.

The plants used in the greenhouse experiments belong to the following species:

| Scientific Name | Common Name |
| --- | --- |
| Chenopodium album | lambsquarters (goosefoot) |
| Echinochloa crus-galli | barnyardgrass |
| Polygonum persicaria | ladysthumb |
| Setaria faberii | giant foxtail |
| Solanum nigrum | black nightshade |
| Zea mays | Indian corn |

At application rates of 0.5 or 0.25 kg/ha, the compound 5.12 (Table 5) had a very good activity against the above-mentioned mono- and dicotyledonous harmful plants and very good tolerability in maize when applied post-emergence.

We claim:

1. A hetaroyl compound of the formula I

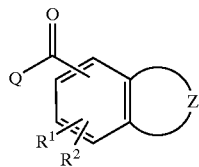

where:

$R^1$ and $R^2$ are each hydrogen, nitro, halogen, cyano, thiocyanato, hydroxyl, mercapto, $C_1$–$C_6$-alkyl, $C_1$–$C_6$-haloalkyl, $C_2$–$C_6$-alkenyl, $C_2$–$C_6$-alkynyl, $C_1$–$C_6$-alkoxy, $C_1$–$C_6$-haloalkoxy, $C_2$–$C_6$-alkenyloxy, $C_2$–$C_6$-alkynyloxy, $C_1$–$C_6$-alkylthio, $C_1$–$C_6$-haloalkylthio, $C_2$–$C_6$-alkenylthio, $C_2$–$C_6$-alkynylthio, $C_1$–$C_6$-alkylsulfinyl, $C_1$–$C_6$-haloalkylsulfinyl, $C_2$–$C_6$-alkenylsulfinyl, $C_2$–$C_6$-alkynylsulfinyl, $C_1$–$C_6$-alkylsulfonyl, $C_1$–$C_6$-haloalkylsulfonyl, $C_2$–$C_6$-alkenylsulfonyl, $C_2$–$C_6$-alkynylsulfonyl, $C_1$–$C_6$-alkoxysulfonyl, $C_1$–$C_6$-haloalkoxysulfonyl, $C_2$–$C_6$-alkenyloxysulfonyl, $C_2$–$C_6$-alkynyloxysulfonyl, phenyl, phenyloxy, phenylthio, phenylsulfinyl or phenylsulfonyl, where the last five substituents may be partially or fully halogenated and may carry one to three of the following groups:

nitro, cyano, hydroxyl, $C_1$–$C_4$-alkyl, $C_1$–$C_4$-haloalkyl, $C_1$–$C_4$-alkoxy, $C_1$–$C_4$-haloalkoxy;

Z is a building block from the group consisting of $Z^1$ to $Z^8$, and $Z^{10}$ to $Z^{12}$ $Z^1$
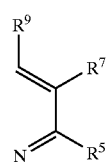

$Z^2$
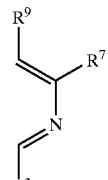

$Z^3$
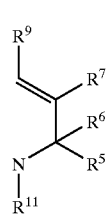

-continued $Z^4$
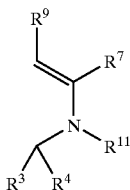

$Z^5$
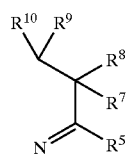

$Z^6$
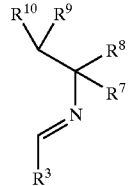

$Z^7$
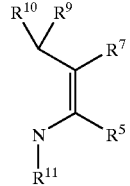

$Z^8$
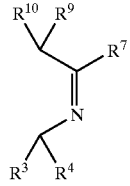

$Z^{10}$
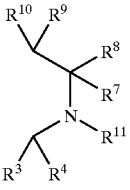

$Z^{11}$
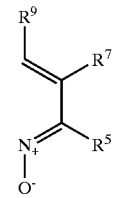

$Z^{12}$
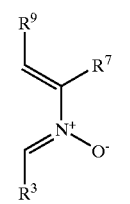

where $R^3$, $R^5$, $R^7$ and $R^9$ are each hydrogen, halogen, $C_1$–$C_4$-alkyl, $C_1$–$C_4$-haloalkyl, $C_1$–$C_4$-haloalkoxy, $C_1$–$C_4$-alkylthio, $C_1$–$C_4$-haloalkylthio, nitro, cyano, hydroxyl, mercapto, $C_2$–$C_4$-alkenyl, $C_2$–$C_4$-alkynyl, $C_2$–$C_4$-alkenyloxy, $C_2$–$C_4$-alkynyloxy, $C_2$–$C_4$-alkenylthio, $C_2$–$C_4$-alkynylthio, $C_1$–$C_4$-alkylsulfinyl, $C_1$–$C_4$-haloalkylsulfinyl, $C_2$–$C_4$-alkenylsulfinyl, $C_2$–$C_4$-alkynylsulfinyl, $C_1$–$C_4$-alkylsulfonyl, $C_1$–$C_4$-haloalkylsulfonyl, $C_2$–$C_4$-alkenylsulfonyl, $C_2$–$C_4$-alkynylsulfonyl, $C_1$–$C_4$-alkoxysulfonyl, $C_1$–$C_4$-haloalkoxysulfonyl, $C_2$–$C_4$-alkenyloxysulfonyl, $C_2$–$C_4$-alkynyloxysulfonyl, —$NR^{12}R^{13}$, —$CO_2R^{12}$, —$CONR^{12}R^{13}$, phenyl, phenoxy, phenylthio, phenylsulfinyl or phenylsulfonyl, where the last five substituents may be partially or fully halogenated and may carry one to three of the following groups:

nitro, cyano, hydroxyl, $C_1$–$C_4$-alkyl, $C_1$–$C_4$-haloalkyl, $C_1$–$C_4$-alkoxy, $C_1$–$C_4$-haloalkoxy;

$R^4$, $R^6$, $R^8$ and $R^{10}$ are each hydrogen, halogen, $C_1$–$C_4$-alkyl, $C_1$–$C_4$-haloalkyl, $C_1$–$C_4$-haloalkoxy, $C_1$–$C_4$-alkylthio or $C_1$–$C_4$-haloalkylthio; or a —$CR^3R^4$-, —$CR^5R^6$-, —$CR^7R^8$- or —$CR^9R^{10}$-unit may be replaced by C=O or C=$NR^{13}$;

$R^{11}$ is hydrogen, $C_1$–$C_6$-alkyl, $C_1$–$C_6$-haloalkyl, $C_3$–$C_6$-alkenyl, $C_3$–$C_6$-alkynyl, $C_1$–$C_6$-alkylcarbonyl, $C_1$–$C_6$-haloalkylcarbonyl, —$CO_2R^{12}$, $CONR^{12}R^{13}$ or $SO_2R^{12}$;

$R^{12}$ is hydrogen, $C_1$–$C_6$-alkyl, $C_1$–$C_6$-haloalkyl, $C_3$–$C_6$-alkenyl, $C_3$–$C_6$-alkynyl or phenyl, where the last radical may be partially or fully halogenated and may carry one to three of the following radicals:

nitro, cyano, hydroxyl, $C_1$–$C_4$-alkyl, $C_1$–$C_4$-haloalkyl, $C_1$–$C_4$-alkoxy, $C_1$–$C_4$-haloalkoxy;

$R^{13}$ is $C_1$–$C_6$-alkoxy, $C_1$–$C_6$-haloalkoxy, $C_3$–$C_6$-alkenyloxy, $C_3$–$C_6$-alkynyloxy or one of the radicals mentioned under $R^{12}$;

Q is a cyclohexane-1,3dione ring, linked through position 2, of the formula II

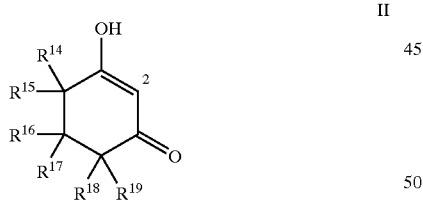

where $R^{14}$, $R^{15}$, $R^{17}$ and $R^{19}$ are each hydrogen or $C_1$–$C_4$-alkyl;

$R^{16}$ is hydrogen, $C_1$–$C_4$-alkyl or $C_3$–$C_4$-cycloalkyl, where the last two groups may carry one to three of the following substituents:

halogen, $C_1$–$C_4$-alkylthio or $C_1$–$C_4$-alkoxy; or is tetrahydropyran-3-yl, tetrahydropyran4-yl, tetrahydrothiopyran-3-yl, 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, where the last 6 radicals may be substituted by one to three $C_1$–$C_4$-alkyl radicals;

$R^{18}$ is hydrogen, $C_1$–$C_4$-alkyl or $C_1$–$C_6$-alkoxycarbonyl; or $R^{16}$ and $R^{19}$ together form a bond or a three- to six-membered carbocyclic ring; or the —$CR^{16}R^{17}$-unit is replaced by C=O, or an agriculturally useful salt thereof.

2. A hetaroyl compound of the formula I as claimed in claim 1, where:

$R^1$ and $R^2$ are each hydrogen, nitro, halogen, cyano, thiocyanato, hydroxyl, mercapto, $C_1$–$C_6$-alkyl, $C_1$–$C_6$-haloalkyl, $C_2$–$C_6$-alkenyl, $C_2$–$C_6$-alkynyl, $C_1$–$C_6$-alkoxy, $C_1$–$C_6$-haloalkoxy, $C_2$–$C_6$-alkenyloxy, $C_2$–$C_6$-alkynyloxy, $C_1$—$C_6$-alkylthio, $C_1$–$C_6$-haloalkylthio, $C_2$–$C_6$-alkenylthio, $C_2$–$C_6$-alkynylthio, $C_1$–$C_6$-alkylsulfinyl, $C_1$–$C_6$-haloalkylsulfinyl, $C_2$–$C_6$-alkenylsulfinyl, $C_2$–$C_6$-alkynylsulfonyl, $C_1$–$C_6$-alkylsulfonyl, $C_1$–$C_6$-haloalkylsulfonyl, $C_2$–$C_6$-alkenylsulfonyl, $C_2$–$C_6$-alkynylsulfonyl, $C_1$–$C_6$-alkoxylsulfonyl, $C_1$–$C_6$-haloalkoxylsulfonyl, $C_2$–$C_6$-alkenyloxysulfonyl, $C_2$–$C_6$-alkynyloxysulfonyl, phenyl, phenyloxy, phenylthio, phenylsulfinyl or phenylsulfonyl, where the last five substituents may be partially or fully halogenated and may carry one to three of the following groups: nitro, cyano, hydroxyl, $C_1$–$C_4$-alkyl, $C_1$–$C_4$-haloalkyl, $C_1$–$C_4$-alkoxy, $C_1$–$C_4$-haloalkoxy;

Z is a building block from the group consisting of $Z^1$ to $Z^8$, and $Z^{10}$ to $Z^{12}$

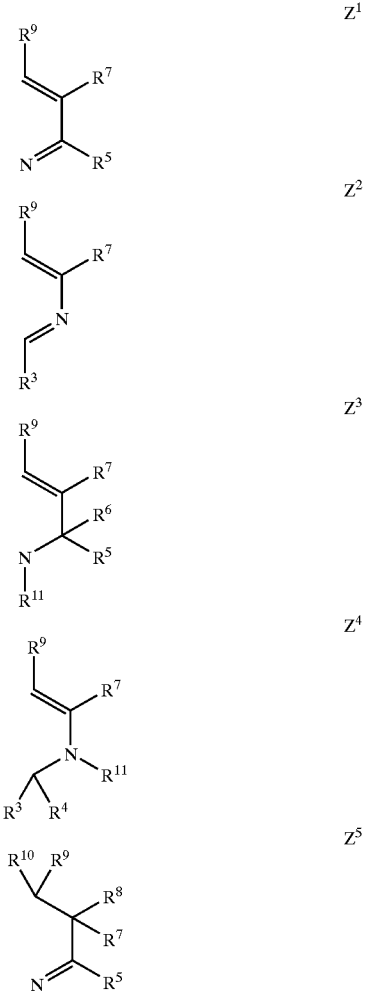

-continued $Z^6$ $Z^7$ $Z^8$ $Z^{10}$ $Z^{11}$ $Z^{12}$ where $R^3$, $R^5$, $R^7$ and $R^9$ are each hydrogen, halogen, $C_1$–$C_4$-alkyl, $C_1$–$C_4$-haloalkyl, $C_1$–$C_4$-haloalkoxy, $C_1$–$C_4$-alkylthio, $C_1$–$C_4$-haloalkylthio, nitro, cyano, hydroxyl, mercapto, $C_2$–$C_4$-alkenyl, $C_2$–$C_4$-alkynyl, $C_2$–$C_4$-alkenyloxy, $C_2$–$C_4$-alkynyloxy, $C_2$–$C_4$-alkenylthio, $C_2$–$C_4$-alkynylthio, $C_1$–$C_4$-alkylsulfinyl, $C_1$–$C_4$-haloalkylsulfinyl, $C_2$–$C_4$-alkenylsulfinyl, $C_2$–$C_4$-alkynylsulfinyl, $C_1$–$C_4$-alkylsulfonyl, $C_1$–$C_4$-haloalkylsulfonyl, $C_2$–$C_4$-alkenylsulfonyl, $C_2$–$C_4$-alkynylsulfonyl, $C_1$–$C_4$-alkoxysulfonyl, $C_1$–$C_4$-haloalkoxysulfonyl, $C_2$–$C_4$-alkenyloxysulfonyl, $C_2$–$C_4$-alkynyloxysulfonyl, —$NR^{12}R^{13}$, —$CO_2R^{12}$, —$CONR^{12}R^{13}$, phenyl, phenoxy, phenylthio, phenylsulfinyl or phenylsulfonyl, where the last five substituents may be partially or fully halogenated and may carry one to three of the following groups: nitro, cyano, hydroxyl, $C_1$–$C_4$-alkyl, $C_1$–$C_4$-haloalkyl, $C_1$–$C_4$-alkoxy, $C_1$–$C_4$-haloalkoxy;

$R^4$, $R^6$, $R^8$ and $R^{10}$ are each hydrogen;

$R^{11}$ is hydrogen, $C_1$–$C_6$-alkyl, $C_1$–$C_6$-haloalkyl, $C_3$–$C_6$-alkenyl, $C_3$–$C_6$-alkynyl, $C_1$–$C_6$-alkylcarbonyl, $C_1$–$C_6$-haloalkylcarbonyl, —$CO_2R^{12}$, —$CONR^{12}R^{13}$ or $SO_2R^{12}$;

$R^{12}$ is hydrogen, $C_1$–$C_6$-alkyl, $C_1$–$C_6$-haloalkyl, $C_3$–$C_6$-alkenyl, $C_3$–$C_6$-alkynyl or phenyl, where the last radical may be partially or fully halogenated and may carry one to three of the following radicals: nitro, cyano, hydroxyl, $C_1$–$C_4$-alkyl, $C_1$–$C_4$-haloalkyl, $C_1$–$C_4$-alkoxy, $C_1$–$C_4$-haloalkoxy;

$R^{13}$ is $C_1$–$C_6$-alkoxy, $C_1$–$C_6$-haloalkoxy, $C_3$–$C_6$-alkenyloxy, $C_3$–$C_6$-alkynyloxy or one of the radicals mentioned under $R^{12}$.

3. A hetaroyl compound of the formula I as claimed in claim 1, where the variable Z is $Z^1$, $Z^2$, $Z^{11}$ or $Z^{12}$.

4. A hetaroyl compound of the formula I as claimed in claim 1, where the variable Z is $Z^3$, $Z^4$, $Z^5$, $Z^6$, $Z^7$ or $Z^8$.

5. A hetaroyl compound of the formula I as claimed in claim 1, where the variable Z is $Z^{10}$.

6. A hetaroyl compound of the formula I as claimed in claim 1, wherein $R^1$ is nitro, halogen, cyano, thiocyanato, hydroxyl, mercapto, $C_1$–$C_6$-alkyl, $C_1$–$C_6$-haloalkyl, $C_2$–$C_6$-alkenyl, $C_2$–$C_6$-alkynyl, $C_1$–$C_6$-alkoxy, $C_1$–$C_6$-haloalkoxy, $C_2$–$C_6$-alkenyloxy, $C_2$–$C_6$-alkynyloxy, $C_1$–$C_6$-alkylthio, $C_1$–$C_6$-haloalkylthio, $C_2$–$C_6$-alkenylthio, $C_2$–$C_6$-alkynylthio, $C_1$–$C_6$-alkylsulfinyl, $C_1$–$C_6$-haloalkylsulfinyl, $C_2$–$C_6$-alkenylsulfinyl, $C_2$–$C_6$-alkynylsulfinyl, $C_1$–$C_6$-alkylsulfonyl, $C_1$–$C_6$-haloalkylsulfonyl, $C_2$–$C_6$-alkenylsulfonyl, $C_2$–$C_6$-alkynylsulfonyl, $C_1$–$C_6$-alkoxysulfonyl, $C_1$–$C_6$-haloalkoxysulfonyl, $C_2$–$C_6$-alkenyloxysulfonyl, $C_2$–$C_6$-alkynyloxysulfonyl, phenyl, phenyloxy, phenylthio, phenylsulfinyl or phenylsulfonyl, where the last five substituents may be partially or fully halogenated and may carry one to three of the following groups: nitro, cyano, hydroxyl, $C_1$–$C_4$-alkyl, $C_1$–$C_4$-haloalkyl, $C_1$–$C_4$-alkoxy, $C_1$–$C_4$-haloalkoxy, and $R^2$ is hydrogen or one of the radicals mentioned under $R^1$.

7. A hetaroyl compound of the formula I as claimed in claim 1, or its N-oxide (formula Ia')

Ia

Ia'

8. A hetaroyl compound of the formula I as claimed in claim 1, or its N-oxide (formula Ib')

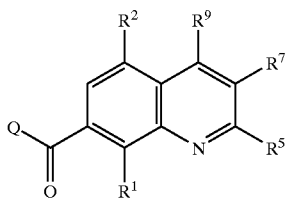

Ib

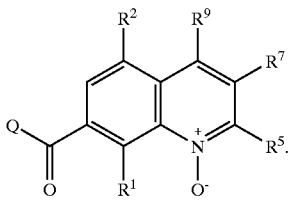

Ib'

9. A hetaroyl compound of the formula I as claimed in claim 1, or its N-oxide (formula Ic')

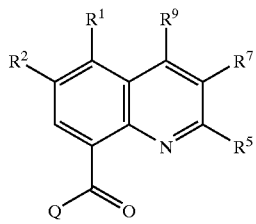

Ic

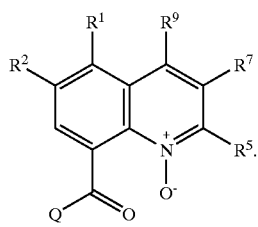

Ic'

10. A hetaroyl compound of the formula I as claimed in claim 1, or its N-oxide (formula Id')

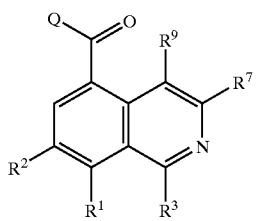

Id

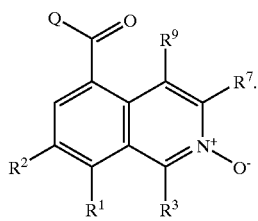

Id'

11. A hetaroyl compound of the formula I as claimed in claim 1, or its N-oxide (formula Ie')

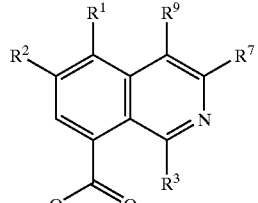

Ie

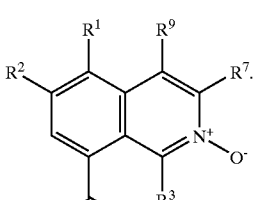

Ie'

12. A process for preparing a compound of the formula I as claimed in claim 1, which comprises acylating the unsubstituted or substituted cyclohexane-1,3dione with an activated carboxylic acid IIIa or with a carboxylic acid IIIb

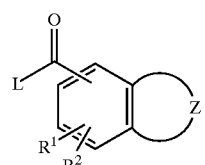

IIIa

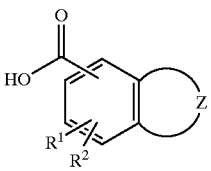

IIIb where the variables $R^1$, $R^2$ and Z are as defined in claim 1 and L is a nucleophilically replaceable leaving group and the acylation product is rearranged in the presence of a catalyst to give the compounds I.

13. A herbicidal composition comprising a herbicidally active amount of at least one hetaroyl compound of the formula I or of an agriculturally useful salt of I as claimed in claim 1 and at least one inert liquid and/or solid carrier and, optionally, at least one surfactant.

14. A process for preparing a herbicidally active composition as claimed in claim 13, which comprises mixing a herbicidally active amount of at least one hetaroyl compound of the formula I or of an agriculturally useful salt of I as claimed in claim 1 and at least one inert liquid and/or solid carrier and, optionally, at least one surfactant.

15. A method for controlling undesirable plant growth, which comprises allowing a herbicidally active amount of at least one hetaroyl compound of the formula I or of an agriculturally useful salt of I as claimed in claim 1 to act on plants, their habitat or on seeds.

16. A hetaroyl compound of the formula I as claimed in claim 1, wherein $R^1$ is nitro, halogen, hydroxyl, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylsulfonyl, $C_1$–$C_6$-haloalkylsulfonyl or phenyl, where the last radical is unsubstituted or may carry one to three halogens and/or a nitro group, a cyano radical, or a methyl, trifluoromethyl, methoxy or trifluoromethoxy substituent;

$R^2$ is hydrogen, halogen or $C_1$–$C_6$-alkyl.

17. A hetaroyl compound of the formula Ia as claimed in claim 7, where $R^1$ is nitro, halogen, hydroxyl, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylsulfonyl, $C_1$–$C_6$-haloalkylsulfonyl or phenyl, where the last radical is unsubstituted or may carry one to three halogens and/or a nitro group, a cyano radical, or a methyl, trifluoromethyl, methoxy or trifluoromethoxy substituent;

$R^2$ hydrogen, halogen or $C_1$–$C_6$-alkyl.

18. A hetaroyl compound of the formula Ia as claimed in claim 7, where $R^2$ is hydrogen;

$R^{14}$, $R^{15}$, $R^{18}$ and $R^{19}$ are each methyl;

the —$CR^{16}R^{17}$-unit is replaced by C=O.

* * * * *

UNITED STATES PATENT AND TRADEMARK OFFICE
CERTIFICATE OF CORRECTION

PATENT NO. : 6,479,436 B1
DATED : November 12, 2002
INVENTOR(S) : Otten et al.

It is certified that error appears in the above-identified patent and that said Letters Patent is hereby corrected as shown below:

Column 61,
Line 41, "1,3dione" should be -- 1,3-dione --;
Line 60, "tetrahydropyran4-yl" should be -- tetrahydropyran-4-yl --.

Column 62,
Line 9, "$C_{1-6}$-" should be -- $C_1$-$C_6$- --.

Column 66,
Line 23, "1,3dione" should be -- 1,3-dione --.

Signed and Sealed this

Eighteenth Day of March, 2003

JAMES E. ROGAN
*Director of the United States Patent and Trademark Office*